(12) United States Patent
Nelson et al.

(10) Patent No.: US 6,608,187 B2
(45) Date of Patent: Aug. 19, 2003

(54) $C_1$ BACTERIOPHAGE LYTIC SYSTEM

(75) Inventors: Daniel C. Nelson, New York, NY (US); Vincent A. Fischetti, West Hempstead, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/863,766

(22) Filed: May 23, 2001

(65) Prior Publication Data

US 2002/0058027 A1 May 16, 2002

Related U.S. Application Data

(60) Provisional application No. 60/206,530, filed on May 23, 2000.

(51) Int. Cl.[7] .................. C07H 19/00; C07K 11/00; C12N 75/09; C12N 15/52; C12N 15/75
(52) U.S. Cl. .................. 536/23.1; 536/23.2; 536/23.7; 530/350; 435/69.1; 435/320.1; 435/471; 435/69.2; 435/472; 435/5; 424/185.1; 424/190.1; 424/234.1; 424/244.1; 424/9.1
(58) Field of Search ............ 424/185.1, 190.1, 424/234.1, 243.1, 264.1, 9.1; 435/5, 472, 320.1, 471, 69.1, 69.2; 536/23.1, 23.2, 23.7; 514/2; 530/350

(56) References Cited

U.S. PATENT DOCUMENTS

| 4,957,686 A | 9/1990 | Norris .................. 424/50 |
| 5,604,109 A | 2/1997 | Fischetti et al. ........... 435/7.34 |
| 5,688,501 A | 11/1997 | Merril et al. ............. 424/93.6 |
| 5,985,271 A | 11/1999 | Fischetti et al. ........... 424/94.1 |
| 6,017,528 A | 1/2000 | Fischetti et al. ........... 424/94.1 |
| 6,056,954 A | 5/2000 | Fischetti et al. ........... 424/94.1 |

FOREIGN PATENT DOCUMENTS

WO    WO 95/31562 A1 * 11/1995

OTHER PUBLICATIONS

Smith et al. J. Bacteriology 1998, vol. 180, pp. 2531–2540.*
Wang et al. Annu. Rev. Microbiol. 2000, vol. 54, pp. 799–825.*
Loessner et al., Journal of Bacteriology 1999, 181(15):4452–4460.
Fischetti et al., Journal of Experimental Medicine 1971, 133(5):11050–1117.
Krause, Journal of Experimental Medicine 1957, 106(3):365–384.
Maxted, J. Gen. Microbiol. 1957, 16(3):584–595.
Raina, Journal of Bacteriology 1981, 145(1):661–663.
Cohen et al., Applied Microbiology 1975, 29(2):175–178.
Young et al., Trends in Microbiology 2000, 8(3):120–128.
Young, Microbiological Reviews 1992, 56(3):430–481.
Ward et al. Genbank NCBI 1996.

* cited by examiner

Primary Examiner—James Housel
Assistant Examiner—Bao Qun Li
(74) Attorney, Agent, or Firm—Darby & Darby

(57) ABSTRACT

The invention relates to the identification of $C_1$ bacteriophage genes that express protein involved in the lysis of bacterial cells during the phage life cycle, lysin and holin. The invention further relates to methods for lysing certain bacteria using lysin, which are useful for example in the treatment of an oral cavity bacterial infection.

12 Claims, 6 Drawing Sheets

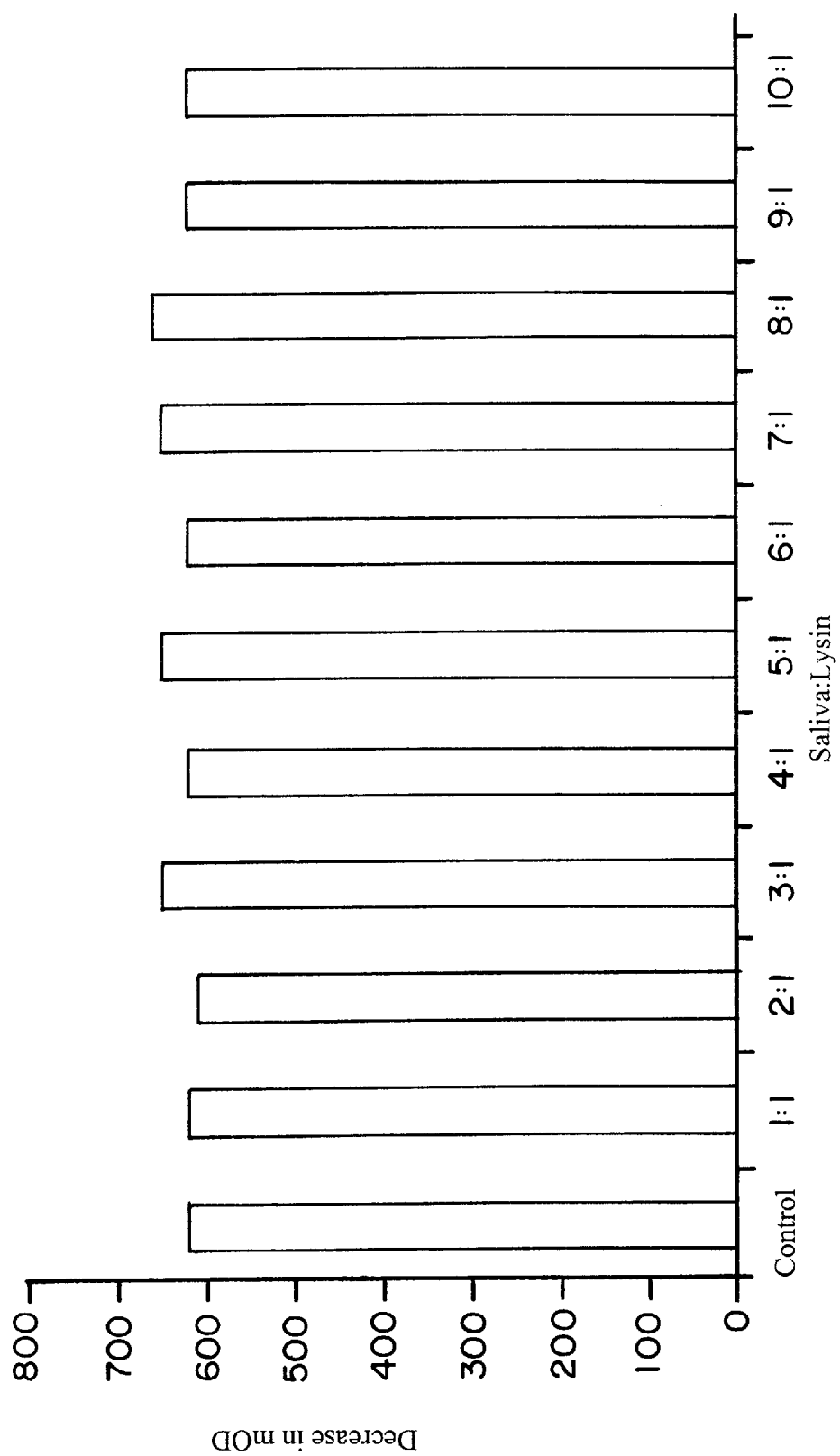

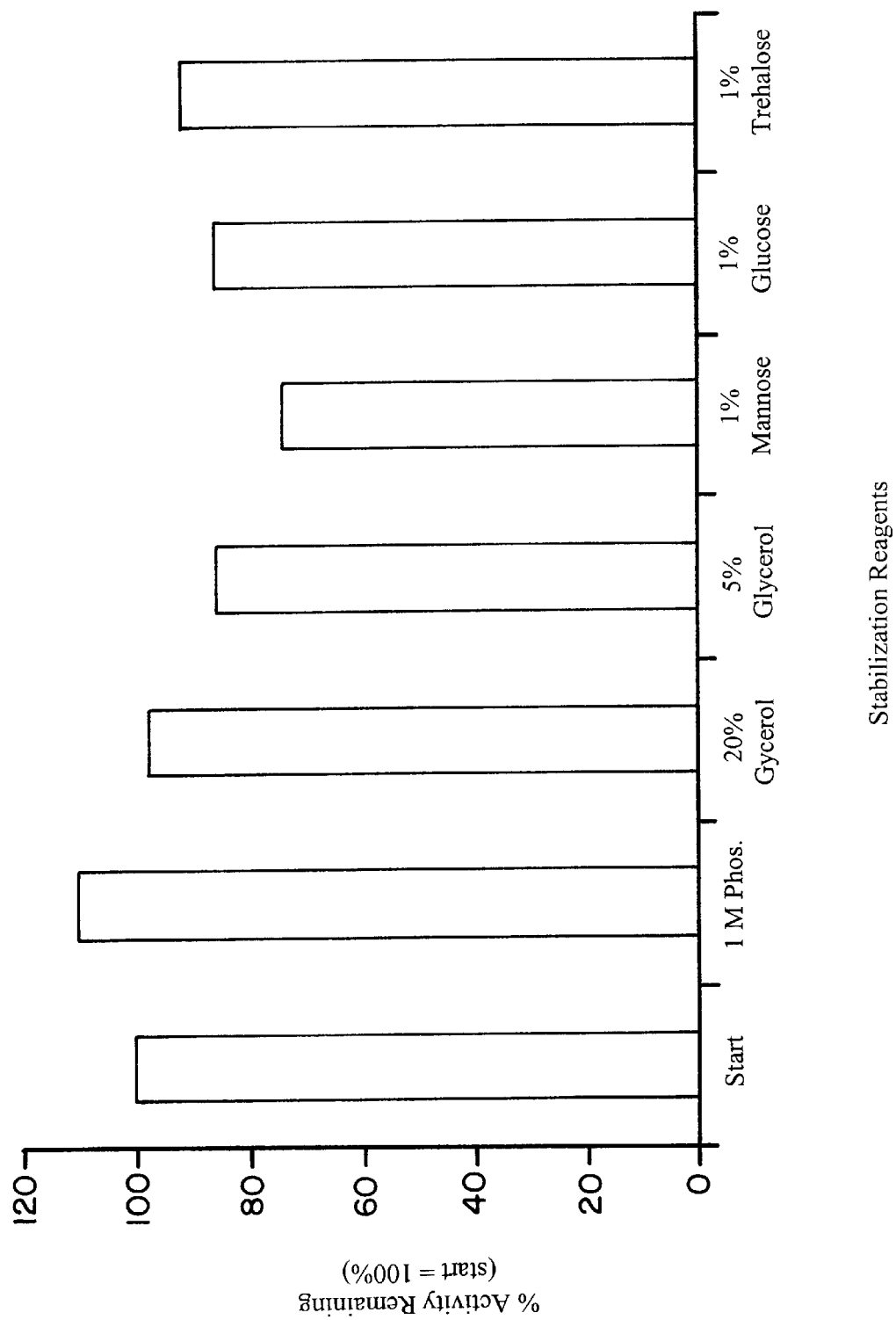

SEQUENCE LISTING

<160> NUMBER OF SEQ ID NOS: 13

<210> SEQ ID NO 1
<211> LENGTH: 222
<212> TYPE: DNA
<213> ORGANISM: C1 bacteriophage

<400> SEQUENCE: 1

```
aatcaaatga gcaagattaa tgtaaacgta gaaatgttt ctggtgtaca aggtttccta      60
ttccataccg atggaaaaga aagttacggt tatcgtgctt ttattaacgg agttgaaatt     120
ggtattaaag acattgaaac cgtacaagga tttcaacaaa ttataccgtc tatcaatatt     180
```

```
agtaagtctg atgtagaggc tatcagaaag gctatgaaaa ag              222
```

<210> SEQ ID NO 2
<211> LENGTH: 74
<212> TYPE: PRT
<213> ORGANISM: C1 bacteriophage

<400> SEQUENCE: 2

```
Asn Gln Met Ser Lys Ile Asn Val Asn Val Glu Asn Val Ser Gly Val
1               5                   10                  15

Gln Gly Phe Leu Phe His Thr Asp Gly Lys Glu Ser Tyr Gly Tyr Arg
            20                  25                  30

Ala Phe Ile Asn Gly Val Glu Ile Gly Ile Lys Asp Ile Glu Thr Val
        35                  40                  45

Gln Gly Phe Gln Gln Ile Ile Pro Ser Ile Asn Ile Ser Lys Ser Asp
    50                  55                  60

Val Glu Ala Ile Arg Lys Ala Met Lys Lys
65                  70
```

<210> SEQ ID NO 3
<211> LENGTH: 360
<212> TYPE: DNA
<213> ORGANISM: C1 bacteriophage
<220> FEATURE:
<221> NAME/KEY: unsure
<222> LOCATION: 27
<223> OTHER INFORMATION: a, t, g or c

<400> SEQUENCE: 3

```
aggccactat gctataataa gtgtagnagg ttttttatga tatatttgtt aatactaaat    60
tccgctgact ttattagcgg tatactcaat ggtattgcat taggtgacat atctagtaag   120
aaactaaaaa aaggaattat tggcaagttg ctgcaatgga ttgttattgc tgtaacaatt   180
acaatgaaac cagttattca tgttgactta cttacatatg ttatcatata ctactatata   240
atggaagtaa tttccattct tgaaaacgtc gcatggtact taccagtgcc aaagaaactg   300
ctaaatgttt tagcacaatt taagaaaata gaaaatgagg taaaatcaaa tgagcaagat   360
```

<210> SEQ ID NO 4
<211> LENGTH: 120
<212> TYPE: PRT
<213> ORGANISM: C1 bacteriophage
<220> FEATURE:
<221> NAME/KEY: unsure
<222> LOCATION: 9
<223> OTHER INFORMATION: unknown

<400> SEQUENCE: 4

```
Arg Pro Leu Cys Tyr Asn Lys Cys Xaa Arg Phe Phe Met Ile Tyr Leu
1               5                   10                  15

Leu Ile Leu Asn Ser Ala Asp Phe Ile Ser Gly Ile Leu Asn Gly Ile
            20                  25                  30

Ala Leu Gly Asp Ile Ser Ser Lys Leu Lys Gly Ile Ile Gly
        35                  40                  45

Lys Leu Leu Gln Trp Ile Val Ile Ala Val Thr Ile Thr Met Lys Pro
    50                  55                  60

Val Ile His Val Asp Leu Leu Thr Tyr Val Ile Tyr Tyr Tyr Ile
65                  70                  75                  80

Met Glu Val Ile Ser Ile Leu Glu Asn Val Ala Trp Tyr Leu Pro Val
                85                  90                  95
```

```
Pro Lys Lys Leu Leu Asn Val Leu Ala Gln Phe Lys Glu Ile Glu Asn
            100                 105                 110
Glu Val Lys Ser Asn Glu Gln Asp
        115                 120
```

<210> SEQ ID NO 5
<211> LENGTH: 22
<212> TYPE: PRT
<213> ORGANISM: C1 bacteriophage

<400> SEQUENCE: 5

```
Lys Ile Asn Val Asn Val Glu Asn Val Ser Gly Val Gln Phe Leu Phe
1               5                   10                  15
His Thr Asp Gly Lys Glu
            20
```

<210> SEQ ID NO 6
<211> LENGTH: 19
<212> TYPE: PRT
<213> ORGANISM: C1 bacteriophage

<400> SEQUENCE: 6

```
Asp Ile Glu Thr Val Gln Gly Phe Gln Gln Ile Ile Pro Ser Ile Asn
1               5                   10                  15
Ile Ser Lys
```

<210> SEQ ID NO 7
<211> LENGTH: 8
<212> TYPE: PRT
<213> ORGANISM: C1 bacteriophage
<220> FEATURE:
<221> NAME/KEY: unsure
<222> LOCATION: 1...2
<223> OTHER INFORMATION: unknown

<400> SEQUENCE: 7

```
Xaa Xaa Tyr Gly Tyr Arg Ala Phe
1               5
```

<210> SEQ ID NO 8
<211> LENGTH: 8
<212> TYPE: PRT
<213> ORGANISM: C1 bacteriophage
<220> FEATURE:
<221> NAME/KEY: unsure
<222> LOCATION: 1
<223> OTHER INFORMATION: unknown

<400> SEQUENCE: 8

```
Xaa Asp Val Glu Ala Ile Arg Lys
1               5
```

<210> SEQ ID NO 9
<211> LENGTH: 6
<212> TYPE: PRT
<213> ORGANISM: Artificial Sequence
<220> FEATURE:
<223> OTHER INFORMATION: thrombin cleavage site

<400> SEQUENCE: 9

```
Leu Val Pro Arg Gly Ser
1               5
```

<210> SEQ ID NO 10
<211> LENGTH: 17

```
<212> TYPE: PRT
<213> ORGANISM: C1 bacteriophage

<400> SEQUENCE: 10

Ala Ala Arg Ala Thr His Ala Ala Tyr Gly Thr Asn Ala Ala Tyr Gly
1               5                   10                  15

Thr

<210> SEQ ID NO 11
<211> LENGTH: 17
<212> TYPE: PRT
<213> ORGANISM: C1 bacteriophage

<400> SEQUENCE: 11

Thr Cys Tyr Thr Thr Asn Cys Cys Arg Thr Cys Asn Gly Thr Arg Thr
1               5                   10                  15

Gly

<210> SEQ ID NO 12
<211> LENGTH: 6
<212> TYPE: PRT
<213> ORGANISM: C1 bacteriophage

<400> SEQUENCE: 12

Lys Ile Asn Val Asn Val
1               5

<210> SEQ ID NO 13
<211> LENGTH: 6
<212> TYPE: PRT
<213> ORGANISM: C1 bacteriophage

<400> SEQUENCE: 13

His Thr Asp Gly Lys Glu
1               5
```

$C_1$ BACTERIOPHAGE LYTIC SYSTEM

This application claims the priority of U.S. Provisional Application No. 60/206,530, filed on May 23, 2000.

FIELD OF THE INVENTION

The invention relates to the identification of $C_1$ bacteriophage genes that express protein involved in the lysis of bacterial cells during the phage life cycle, lysin and holin. The invention further relates to methods for lysing certain bacteria using lysin, which are useful for example in the treatment of an oral cavity bacterial infection.

BACKGROUND OF THE INVENTION

All double stranded DNA bacteriophages contain a lytic system consisting of a holin and at least one peptidoglycan hydrolase or "lysin", which is capable of degrading the bacterial cell wall to allow phage release. In Gram positive bacteria, lysins can be endo-p-N-acetylglucosaminidases or N-acetylmuramidases (lysozymes), which act on the sugar moiety; an endopeptidase, which acts on the peptide cross bridge; or more commonly, an N-acetyhnuramoyl-L-alanine amidase, which hydrolyzes the amide bond connecting the sugar and peptide moieties (for review, see (Young et al., 2000)). Typically, the holin which is expressed in the late stages of infection forms a pore in the cell membrane allowing the lysin to gain access to the cell wall peptidoglycan and resulting in release of progeny phage. Exogenously added lysin can lyse the cell wall of healthy, uninfected cells, producing "lysis from without".

The virulent $C_1$ bacteriophage specifically infects group C streptococci and produces a very powerful lysin (Evans, 1934; Maxted, 1957). Interestingly, the $C_1$ phage lysin has hydrolytic activity against cell walls of group A streptococci as well as group C streptococci (Cohen et al., 1975; Fischetti et al., 1971; Raina, 1981). This unique activity has been exploited as a tool in group A streptococcal studies to isolate surface molecules including M protein (Cohen et al., 1977; Fischetti et al., 1985), to extract DNA from lysed cells, and to make protoplasts when used in a hypertonic solution (Wheeler et al., 1980). The cell wall lysis activity of $C_1$ lysin is also potentially very useful in the treatment of oral cavity bacterial infections.

It is to be noted that the direct introduction of bacteriophages into an animal to prevent or fight diseases has certain drawbacks. Specifically, the bacteria must be in the right growth phase for the phage to attach. Both the bacteria and the phage have to be in the correct and synchronized growth cycles. Additionally, there must be the right number of phages to attach to the bacteria; if there are too many or too few phages, there will either be no attachment or no production of the lysing enzyme. The phage must also be active enough. The phages are also inhibited by many things including bacterial debris from the organism it is going to attack. Further complicating the direct use of bacteriophage to treat bacterial infections is the possibility of immunological reactions, rendering the phage non-functional.

Despite these drawbacks, attempts have been made to treat bacterial diseases with by the use of bacteriophages. U.S. Pat. No. 5,688,501 discloses a method for treating an infectious disease caused by bacteria in an animal with lytic or non-lytic bacteriophages that are specific for particular bacteria. U.S. Pat. No. 4,957,686 discloses a procedure of improved dental hygiene by introducing into the mouth bacteriophages parasitic to bacteria that readily adheres to the salivary pellicle.

$C_1$ lysin containing compositions are also useful in the topical treatment of wounds and burns to the skin. U.S. Pat. No. 6,056,954 discloses methods of the treatment of these injuries by the administration of partially purified $C_1$ lysin to a patient. U.S. Patent No. 6,056,955 discloses methods of treating dermatological infections caused by streptococcal bacteria by administering a semipurified $C_1$ lysin.

U.S. Pat. No. 5,985,271 discloses administration of therapeutic amounts of semipurified lysin to a patient to treat a streptococcal infection of the mouth, throat or nasal passages. U.S. Pat. No. 6,017,528 discloses semipurified $C_1$ lysin compositions for prophylactic and therapeutic treatment of streptococcal infection. However, these compositions comprised relatively impure preparations of the enzyme: the soluble fraction of $C_1$ bacteriophage infected bacterial cell lysates comprises a number of factors in addition to lysin. Thus, these methods suffer from a disadvantage of uncertainty of the amount of lysin enzyme administered, the presence and nature of any contaminants, and the resulting variability in dosages and safety profiles of these lysin preparations. Furthermore, these preparations have lower specific activity values (units of enzyme/gram of protein) due to the presence of other bacterial proteins. Substantially purified material is much more defined than the semipurified material disclosed in the prior art and is therefore much more desirable for ingestable therapeutic compositions. There is a need in the art for highly purified lysin so that it can be characterized, cloned, and used therapeutically.

SUMMARY OF THE INVENTION

The present invention is directed to a homogeneously purified C1 bacteriophage lysin protein (lysin) and a homogeneously purified holin protein (holin). Furthermore, the present invention is directed to both a specifically disclosed lysin and holin, as disclosed in SEQ ID NO:2 and SEQ ID NO:4, respectively. The present invention also includes proteins which are about 70% identical to the amino acid sequences as set forth in SEQ ID NO:2 and SEQ ID NO:4, as well as to pharmaceutical compositions comprising homogeneously purified lysin.

This invention also includes an isolated nucleic acid molecule encoding a Cl bacteriophage lysin protein and an isolated nucleic acid molecule encoding a C1 bacteriophage holin protein. Also included in the present invention are nucleic acids which encode amino acid sequences which are about 70% identical to the amino acid sequence set forth in SEQ ID NO:2 or the amino acid sequence set forth in SEQ ID NO:4. Specifically disclosed nucleic acid molecules whose nucleotide sequences are set forth in SEQ ID NO:1 and SEQ ID NO:2 are also included in this invention.

An expression vector comprising the C1 lysin gene and an expression vector comprising the C1 holin gene are included in the invention, as are host cells comprising one of these expression vectors.

A method of producing lysin protein or holin protein comprising culturing a host cell as mentioned above under conditions which allow the expression of lysin or holin are included in the invention. This method may further comprise purification of lysin or holin to homogeneity.

The present invention also includes a method of degrading streptococci susceptible to lysin. This method involves contacting the bacterial cell wall with lysin. These streptococci may include group A or C streptococci. A method of treating or preventing a streptococcal infection in a patient comprising administration of a pharmaceutical composition comprising lysin is also a part of the invention. The infection treated by this method may include oral cavity infections and may include administration of a lysin containing pharmaceutical composition directly to the oral cavity. Methods of coadministration of a second therapeutic agent in addition to the lysin containing pharmaceutical composition are also a part of this invention.

Anti-holin or an anti-lysin antibodies are included in the present invention.

The present invention also includes a method for detecting group C or group A streptococcal antigens. This method comprises detecting the group C or A streptococcal antigen in a clinical specimen suspected of containing group C or A streptococci contacted with an extraction reagent comprising a lytic amount of homogeneously purified lysin enzyme, thereby releasing group C or A streptococcal antigen into the extraction reagent using an immunological ligand receptor assay.

BRIEF DESCRIPTION OF THE DRAWINGS

FIG. 3. The effect of human saliva on lysin activity.

FIG. 4. The effect of stabilizing agents on lysin.

DETAILED DESCRIPTION

The present invention advantageously provides a homogeneous preparation of $C_1$ phage lysin, which acts as a potent, specific antibiotic.

Discoveries of homogeneously pure lysin, which permitted cloning and sequencing the $C_1$ phage lysin gene, sequencing lysin protein, and recombinant production of recombinant lysin in non-susceptible expression systems form, in part, the basis of this invention.

In addition, to $C_1$ phage lysin, the invention also provides $C_1$ phage holin. This protein has strong pore-forming action in membranes, such as the streptococcus inner membrane.

The term "lysin" as used herein refers to the $C_1$ phage protein that degrades gram-positive bacterial cell walls. As exemplified infra, $C_1$ phage lysin has a predicted molecular mass of about 84 kDa; in a specific embodiment, it has a predicted molecular mass of 8231. However, measurements of lysin's apparent molecular weight, e.g., by gel filtration chromotography, yields a value of about 100 kDa. Other characteristics of lysin include a predicted isoelectric point of 8.25; strong association with hydroxylapatite (requiring elution with 1 M phosphate); irreversible deactivation by ethylmaleimide, iodoacetamide, and hydroxmercuribenzoic acid; reversible deactivation in dithiopyridine, slight deactivation by iodoacetic acid and no deactivation by sodium tetrathiozine. Lysin is also stabilized (kept enzymatically active) bythepresence of reducing agents, including dithiothreitol(DTT), β-mercaptoethanol, cysteine, and glutathione, and in the presence of metal chelators. The predicted molecular weight and isoelectric point can be obtained by use of the Compute pI/Mw algorithm. Access to this algorithm is free of charge at expasy.ch/tools/pi_tool.html on the WorldWide Web.

Lysin of the invention can also be characterized by its antibacterial activity and potency, which are distinct from prior preparations of the protein. In particular, homogeneously purified lysin lyses *Streptococcus gordonii* in addition to group A and group C streptococci. Homogeneously purified lysin is also more potent than previous lysin preparations. The specific activity (activity per gram of protein) of the homogeneous lysin is greater than previous preparations, which were of a lower purity.

Figure 1:
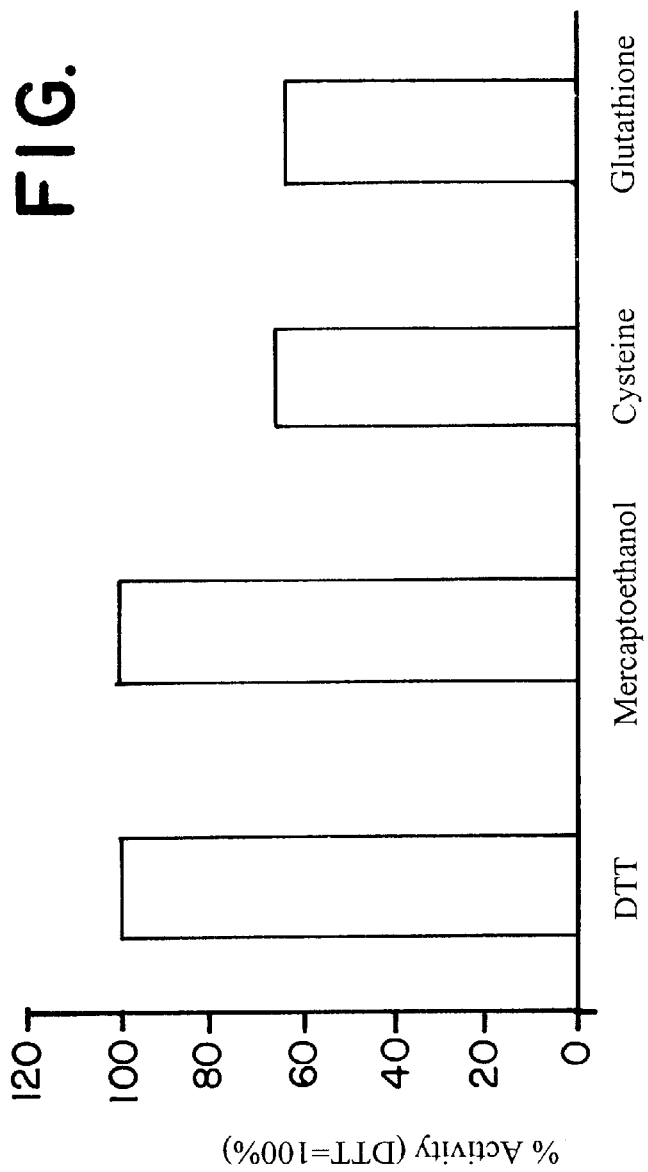
FIG. 1. Effects of Reducing Agents on Lysin Activity.

In a specific embodiment, lysin has an amino acid sequence at least about 70% identical, preferably at least 80% identical, more preferably at least 90% identical, and even more preferably still greater than about 95% identical to the sequence in SEQ ID NO:2. Thus, lysin includes closely related homologs, and particularly variants from other strains of $C_1$ bacteriophage. Lysin of the invention can be further characterized by comprising one or more partial amino acid sequences, as shown in FIG. 1, or any partial sequence of 10 or more contiguous amino acids, preferably 15 or more, and more preferably 20 or more, from the full length sequence in SEQ ID NO:2.

Lysin can be encoded by a nucleic acid having a nucleotide sequence at least about 70% identical to the sequence in SEQ ID NO:1; preferably 80%, more preferably 90%. In a specific aspect, the nucleic acid encodes an amino acid sequence as shown in SEQ ID NO:2; in an even more specific embodiment, the nucleotide sequence is that disclosed in SEQ ID NO: 1.

$C_1$ bacteriophage (or phage) is a phage specific for group C streptococci (Evans, 1934; Maxted, 1997; Moynet et al., 1985; Vereneau et al., 1977). This phage has physical characteristics-polyhedron head about 45×45 nm, base plate, and several short tail fibers—that closely resemble those of the order Caudovirales and the family Podoviridae (T7 phage, P22 phage, F29 phage). Thus, $C_1$ phage, as discovered herein, appears to be the fourth member of the Podoviridae family.

A gram-positive bacterium or bacterial cell wall is susceptible to degradation by lysin of the invention when, upon contact with a lysin preparation, especially homogeneously purified lysin of the invention, the lysin cleaves peptidoglycan in the cell wall. Such activity can be measured by measuring optical density (opaque bacteria suspensions become clear, so optical density decreases), immunoassay (for the presence of bacterial proteins released from the inside of the cell wall after lysin treatment), or by measuring bacterial viability (lysin activity kills the target or susceptible bacteria), to mention a few such techniques. Other enzyme activity assays are described in the examples. "Holin" refers to the $C_1$ phage protein that forms pores, e.g., in the inner lipid bilayer membrane of gram-positive bacteria. Holin pores admit lysin, which, when expressed from lytic phage, degrades the outer wall of bacteria. Holin of the invention is characterized by an apparent molecular mass of about 14 kDa; in a specific embodiment, holin has a predicted mass of 13811 gm/mole. In another embodiment, holin of the invention has at least about 70% sequence identity with the sequence in SEQ ID NO:4, preferably 80%, more preferably 90%, and more preferably still greater than about 95%. In a specific embodiment exemplified, infra, holin has the sequence as depicted in SEQ ID NO:4.

Holin can be encoded by a nucleic acid having a nucleotide sequence at least about 70% identical to the sequence in SEQ ID NO:3, preferably 80%, and more preferably 90%. In a specific embodiment, the nucleic acid encodes an amino acid sequence as depicted in SEQ ID NO:4; in an even more specific embodiment, the nucleotide sequence is that disclosed in SEQ ID NO:3.

The term "homogeneous" and "homogeneously purified" or any grammatical alternatives (purified to homogeneity, etc.) means that, by suitable analytical testing, including polyacrylamide gel electrophoresis, the preparation is free of impurities, or only contains minor impurities that do not interfere with analytical testing of the preparation, e.g., protein sequencing or enzymatic cleavage, or with the protein's native biochemical activity.

As used herein, the term "isolated" means that the referenced material is removed from its native environment, e.g., a cell. Thus, an isolated biological material can be free of some or all cellular components, i.e., components of the cells in which the native material is occurs naturally (e.g., cytoplasmic or membrane component). A material shall be deemed isolated if it is present in a cell extract or if it is present in a heterologous cell or cell extract. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid.

An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Any method which results in a homogeneously purified preparation of lysin or isolated holin are embodied within this invention. Lysin or holin produced, for example, by the methods described in the present application, may be removed from other cellular and cultural components. Chromatographic methods of purification are particularly useful embodiments by which to obtain purified protein. Protein purification columns comprising matrices such as hydroxyapatite, anion exchange resins, cation exchange resins, hydrophobic resins and others may be used to purify lysin or holin. A preferred purification matrix for lysin is hydroxylapetite. Size exclusion chromatography and dialysis may also be used to purify these proteins. Furthermore, these proteins may be fused with an affinity tag such as a polyhistidine (6 or more) tag, a glutathione-S-transferase (GST) tag, a maltose binding tag (malE), a T7 bacteriophage gene 10 peptide tag, a chitin binding domain tag (CBD) or other tags. Affinity tagged lysin or holin proteins may be produced such that the affinity tag is cleavable after purification. That is, a protease cleavage site may be genetically engineered into the region between the tag and the lysin or holin. The tag may be removed from the rest of the protein by incubation with the protease which recognizes the cleavage site. For example, thrombin may be incubated with a tagged holin or lysin which comprises the amino acid sequence LVPRGS (SEQ ID NO:9) after the tag.

The proteins of the invention may be expressed by several methods. Lysin and holin maybe expressed recombinantly by recombinant bacteria, such as *E. coli* strains that are not affected by lysin and/or holin. The expression of lysin should not be problematic in these embodiments since it has only been demonstrated to be active against the cell walls of susceptible bacteria, such as group A and group C streptococci, and not other bacteria like *E. coli*. The expression of holin should not be problematic either. This protein is capable of inserting itself into cell membranes. However, most of the structural integrity of a bacterial cell is derived from the cell wall. Perturbations in the cell membrane are not expected to have a very deleterious effect on cell structure. Expression of these proteins may also be accomplished in the cell lysates of, for example, bacteria or eukaryotic cells such as yeast or rabbit reticulocyte lysates. Additionally, group A and group C streptococci infected with bacteriophage $C_1$ are also a useful source of lysin. Lysin protein which is released from a population of infected cells may be collected and used for any other applications embodied by this invention.

The enzymatic activity of lysin protein cleaves peptidoglycan in the cell walls of group A and C streptococci. This activity may be measured in vitro, in which aqueous opaque suspensions containing group A or group C streptococci or isolated cell wall preparations are subjected to lysin enzymatic digestion. The progress of the reaction may be monitored by measuring the optical density of the enzymatic reaction. As the reaction progresses, the optical density decreases. Measurement of the reaction velocity may be performed by calculating the rate of decrease in optical density. The data gathered from reaction velocity measurements may be used to calculate the number of units of enzyme in a particular enzyme preparation.

Holin has no enzymatic activity. The function of holin during the lifecycle of the $C_1$ bacteriophage is to penetrate the cell membrane of the host bacterial cell. Thus the susceptibility of a bacterium of interest to holin may be tested by methods comprising contacting the cell membrane with the protein and detecting cell membrane penetration. This may be accomplished by a number of acceptable methods. Such methods may include exposing said bacteria to holin and detecting membrane which comprises a detectable label such as a radioisotope and detecting labeled holin in the membrane. After removal of nonspecifically bound holin, the quantity of specifically bound protein may be assessed by detecting the label. Furthermore, other methods comprising the use of unlabeled holin wherein cell membrane binding is detected immunologically (with an anti-holin antibody) are also possible embodiments of the present invention. Antibody/holin complexes may be detected with a labeled secondary antibody. Other methods for detecting holin insertion in membrane include measuring leakage of molecules in or out of the membrane, and conductivity of the membrane in the presence and absence of holin.

General Molecular Biology Techniques and Definitions

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation. "Amplification" of DNA as used herein denotes the use of polymerase chain reaction (PCR) to increase the concentration of a particular DNA sequence within a mixture of DNA sequences. For a description of PCR see Saiki et al., Science, 239:487, 1988.

Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of $C_1$ holin or $C_1$ lysin, or to detect the presence of nucleic acids encoding $C_1$ holin or $C_1$ lysin. In a further embodiment, an oligonucleotide of the invention can form a triple helix with a $C_1$ holin or $C_1$ lysin DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The ability of a nucleic acid molecule to hybridize to another is a suitable measure of the level of sequence homology between the two molecules. The binding of nucleic acid molecules in a composition to a nucleic acid molecule of interest is a suitable test for the presence of nucleic acid molecules with a certain degree of homology to the nucleic acid molecule of interest. Conditions of temperature and ionic strength determine the "stringency" of the hybridization. For preliminary screening for homologous nucleic acids, low stringency hybridization conditions, corresponding to a Tm (melting temperature) of 55 C, can be used, e.g., 5× SSC, 0.1% SDS, 0.25% milk, and no formamide; or 30% formamide, 5× SSC, 0.5% SDS). Moderate stringency hybridization conditions correspond to a higher Tm, e.g., 40% formamide, with 5× or 6× SSC. High stringency hybridization conditions correspond to the highest Tm, e.g., 50% formamide, 5× or 6× SSC. SCC is a 0.15M Nacl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a possible embodiment, the term "standard hybridization conditions" refers to a Tm of 55° C., and utilizes conditions as set forth above. In a preferred embodiment, the Tm is 60° C.; in a more preferred embodiment, the Tm is 65° C. In a possible embodiment, "high stringency" refers to hybridization and/or washing conditions at 68° C. in 0.2× SSC, at 42 C in 50% formamide, 4× SSC, or under conditions that afford levels of hybridization equivalent to those observed under either of these two conditions.

A "coding sequence" or a sequence "encoding" or "coding for" an expression product, such as a RNA or protein, is a nucleotide sequence that, when expressed, results in the production of that RNA or protein, i.e., the nucleotide sequence encodes an amino acid sequence for a protein.

A coding sequence for a protein may include a start codon (usually ATG) and a stop codon. A nucleotide sequence may also "encode" or "code for" a gene.

The term "gene" or "structural gene" means a DNA sequence that encodes or corresponds to a particular sequence of amino acids which comprise all or part of one or more proteins, and may or may not include regulatory DNA sequences, such as promoter sequences, that determine for example the conditions under which the gene is expressed. The transcribed region of a gene can include 5'- and 3'-untranslated regions (UTRs) and introns in addition to the translated (coding) region.

A "disrupted gene" refers to a gene, as described above, wherein a segment of DNA is inserted into the coding sequence of that gene thereby breaking the continuity, and possibly deleting a portion of the coding sequence.

A gene is "inactivated" when it is modified or acted on in such a way as to prevent the expression of a product which is as functional as the product from the same, unmodified gene.

A "replicon" is any genetic element (e.g., plasmid, chromosome, virus) that functions as an autonomous unit of DNA replication in vivo, i.e., capable of replication under its own control.

Proteins and enzymes are made in the host cell using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids which form the protein or enzyme. An "amino acid sequence" is any chain of two or more amino acids. Each amino acid is represented in DNA or RNA by one or more triplets of nucleotides. Each triplet forms a codon, corresponding to an amino acid. For example, the amino acid lysine (Lys) can be coded by the nucleotide triplet or codon AAA or by the codon AAG. (The genetic code has some redundancy, also called degeneracy, meaning that most amino acids have more than one corresponding codon.) Because the nucleotides in DNA and RNA sequences are read in groups of three for protein production, it is important to begin reading the sequence at the correct amino acid, so that the correct triplets are read. The way that a nucleotide sequence is grouped into codons is called the "reading frame." As used herein, the term "oligonucleotide" refers to a nucleic acid, generally of at least 10, preferably at least 15, and more preferably at least 17 nucleotides, preferably no more than 100 nucleotides, that is hybridizable to a genomic DNA molecule, a cDNA molecule, or an mRNA molecule encoding a gene, mRNA, cDNA, or other nucleic acid of interest. DNA sequence data for the lysin gene may be obtained by sequencing the PCR amplified fragment after insertion into a suitable plasmid. The entire sequence of lysin and its neighboring genes, in the $C_1$ bacteriophage genome, may be obtained by use of the chromosome walking technique. This technique involves extending the sequence data corresponding to a region of a chromosome by successively sequencing regions that overlap the ends of previously sequenced areas. By this technique the holin gene, which is adjacent to the lysin gene, was identified.

The term "identity" or "homology" refers to the number of nucleotide or amino acid matches between two or more DNA sequences or proteins, over a defined length of the DNA sequence or protein, as determined by sequence comparison algorithms such as BLASTN or BLASTP, respectively. There are several sources on the internet at which programs using these algorithms may be accessed without cost. One such site is the National Center for Biotechnology Information at ncbi.nlm.nih.gov/on the WorldWide Web.

The present invention contemplates homologues of holin and lysin that are at least 70% identical in their nucleotide sequences or amino acid sequences. Homologues which are more than 70% identical are also included in the embodiments of the present invention. Calculations of amino acid or nucleotide identity may be performed by use of the BLASTP or BLASTN computer applications, respectively.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. Generally, a host cell, which has been transformed by a piece of DNA, will stably maintain the presence that DNA molecule in the progeny cells of successive generations.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme.

A "clone" is a population of cells derived from a single cell.

The term "heterologous" refers to a combination of elements not naturally occurring. For example, heterologous DNA refers to DNA not naturally located in the cell, or in a chromosomal site of the cell. Heterologous DNA may include a gene foreign to the cell or a gene native to the cell but as A heterologous expression regulatory element is a such an element operatively associated with a different gene than the one it is operatively associated with in nature. In the context of the present invention, a $C_1$ holin or $C_1$ lysin gene is heterologous to the vector DNA in which it is inserted for cloning or expression, and it is heterologous to a host cell containing such a vector, in which it is expressed, e.g., a CHO cell.

A "vector" is a replicon, such as plasmid, phage or cosmid, to which another DNA segment may be attached so as to bring about the replication of the attached segment.

A wide variety of host/expression vector combinations (i.e., expression systems) may be employed in expressing the DNA sequences of this invention. Furthermore, expression of $C_1$ holin or $C_1$ lysin may be done in either a whole cell or a cell lysate. Cell lysates in which expression may be preformed may include rabbit reticulocyte lysate systems. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., Gene 67:31-40, 1988), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. In addition, various tumor cells lines can be used in expression systems of the invention. Host cells which are particularly useful include BL21DE3 *E. coli*. When transformed with a plasmid bearing a gene which is operably associated with the T7 promoter, the endogenously expressed T7 RNA polymerase causes very high levels of expression of the gene.

Yeast expression systems can also be used according to the invention to express any protein of interest. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamHI, SacI, KpnI, and HindIII cloning site, N-terminal peptide purified with Pro Bond resin and cleaved with enterokinase; Invitrogen), to mention just two, can be employed according to the invention.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of or "operably associated with" transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as an mRNA or a protein. The expression product itself, e.g. the resulting mRNA or protein, may also be said to be "expressed" by the cell. An expression product can be characterized as intracellular, extracellular or secreted. The term "intracellular" means something that is inside a cell. The term "extracellular" means something that is outside a cell.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. No. 5,385,839 and No. 5,168,062), the SV40 early promoter region (Benoist and Chambon, 1981, Nature 290:304-310), the promoter contained in the 3' long terminal repeat of Rous sarcoma virus (Yamamoto, et al., Cell 22:787-797, 1980), the herpes thymidine kinase promoter (Wagner et al., Proc. Natl. Acad. Sci. U.S.A. 78:1441-1445, 1981), the regulatory sequences of the metallothionein gene (Brinster et al., Nature 296:39-42, 1982); prokaryotic expression vectors such as the β-lactamase promoter (Villa-Komaroff, et al., Proc. Natl. Acad. Sci. U.S.A. 75:3727-3731, 1978), or the tac promoter (DeBoer, et al., Proc. Natl. Acad. Sci. U.S.A. 80:21-25, 1983); see also "Useful proteins from recombinant bacteria" in Scientific American, 242:74-94, 1980; promoter elements from yeast or other fungi such as the Gal 4 promoter, the ADC (alcohol dehydrogenase) promoter, PGK (phosphoglycerol kinase) promoter, alkaline phosphatase promoter.

Detection of Streptococcal Infections

Impure lysin preparations are presently used to lyse group A streptococci to expose a specific bacterial antigen for diagnostic testing (U.S. Pat. No. 5,604,109). Once exposed, the antigen readily binds a specific antibody.

Lysin, homogeneously prepared in accordance with the invention, can be used in such diagnostic applications, particularly where greater quantitation or reduction in cross-reacting impurities improves the testing results. These preparations, maintained in enzymatically active form, can be prepared in diagnostic kits, e.g., by storage in an appropriate container (glass or plastic vial, in solution or as a dried preparation), along with a detection system, e.g., a bacteriol antigen-specific immunoassay. Diagnostic kits of the invention may also include instructions for use.

Described herein is a diagnostic test for the identification of group A and group C streptococci from infected tissues. The test may be performed in a single step and provides the user with an answer in less than 5 minutes without the need for complicated equipment or experience. This permits the test to be performed in both the doctor's office as well as the home.

Thus, the doctor is able to determine the course of treatment rapidly without the need to delay 24 to 48 hours for the results of conventional assays. The assay depends on the rapid and efficient extraction of antigen from the streptococcus in the specimen rather than waiting for the organisms to grow on culture media for identification. The activity of the extracting enzyme and the specificity of the antibody probe allow the invention assay to be nearly as accurate and as sensitive as the conventional culture test.

In accordance with the present invention, a test kit will be provided for the accurate and rapid identification of group A or group C streptococci from biological specimens. The specimen is collected onto an applicator stick fitted at one end with a fiber swab. The infected area is swabbed to transfer the organisms from the infected tissue to the swab. The swab is then transferred to a solution containing the homogeneously purified lysin enzyme in a buffered solution. The contact time between the swab and lysin enzyme is less than 30 minutes and preferably less than 6 minutes. The assay can be performed at room temperatures (21° C. to 29° C.). The enzyme digests the cell wall of any group A or group C streptococci present in the swab and releases the group carbohydrate in solution. An important feature of the invention is the fact that the organisms trapped in the matrix of the fibers will also be digested thus, the organisms do not need to be released in solution for the digestion to occur. Since the enzyme solution exhibits no proteolytic activity, the indicator reagent (antibody specific for the group carbohydrate) may be present in the extracting solution during the extraction process. As antigen is released from a swab containing group A or group C streptococci, the antibody will react with the antigen. Another feature of the invention is the high activity of this enzyme for the group A or group C streptococcal cell wall allowing for complete release of the cell wall antigen in less than minutes.

Antibodies

According to the invention, lysin or holin polypeptides produced recombinantly or by chemical synthesis, and fragments or other derivatives or analogs thereof, including fusion proteins, may be used as an immunogen to generate antibodies that recognize the lysin or holin polypeptides. Such antibodies include but are not limited to polyclonal, monoclonal, chimeric, single chain, Fab fragments, and an Fab expression library. The anti-lysin or anti-holin antibodies of the invention may be cross reactive, e.g., they may recognize lysin or holin polypeptides from different species. Polyclonal antibodies have greater likelihood of cross reactivity.

Various procedures known in the art may be used for the production of polyclonal antibodies to lysin or holin polypeptides or derivative or analog thereof. For the production of antibody, various host animals can be immunized by injection with lysin or holin polypeptides, or a derivative (e.g., fragment or fusion protein) thereof, including but not limited to rabbits, mice, rats, sheep, goats, etc. In one embodiment, the lysin or holin polypeptides or fragments thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and Corynebacterium parvum.

For preparation of monoclonal antibodies directed toward the lysin or holin polypeptides, or fragments, analogs, or derivatives thereof, any technique that provides for the production of antibody molecules by continuous cell lines in culture may be used. These include but are not limited to the hybridoma technique originally developed by Kohler and Milstein (Nature 256:495-497, 1975), as well as the trioma technique, the human B-cell hybridoma technique (Kozbor et al., Immunology Today 4:72, 1983; Cote et al., Proc. Natl. Acad. Sci. U.S.A. 80:2026-2030, 1983), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published Dec. 28, 1989). In fact, according to the invention, techniques developed for the production of "chimeric antibodies" (Morrison et al., J. Bacteriol. 159:870, 1984; Neuberger et al., Nature 312:604-608, 1984; Takeda et al., Nature 314:452-454, 1985) by splicing the genes from a mouse antibody molecule specific for a lysin or holin polypeptides together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476,786 and 5,132,405 to Huston; U.S. Pat. No. 4,946,778) can be adapted to produce lysin or holin polypeptide-specific single chain antibodies. Indeed, these genes can be delivered for expression in vivo. An additional embodiment of the invention utilizes the techniques described for the construction of Fab expression libraries (Huse et al., Science 246:1275-1281, 1989) to allow rapid and easy identification of monoclonal Fab fragments with the desired specificity for lysin or holin polypeptides, or its derivatives, or analogs.

Antibody fragments which contain the idiotype of the antibody molecule can be generated by known techniques. For example, such fragments include but are not limited to: the F(ab¢)2 fragment which can be produced by pepsin digestion of the antibody molecule; the Fab¢ fragments which can be generated by reducing the disulfide bridges of the F(ab¢)2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a lysin or holin polypeptide, one may assay generated hybridomas for a product which binds to a lysin or holin polypeptide fragment containing such epitope. For selection of an antibody specific to a lysin or holin polypeptide from a particular species of animal, one can select on the basis of positive binding with lysin or holin polypeptides expressed by or isolated from cells of that species of animal.

The foregoing antibodies can be used in methods known in the art relating to the localization and activity of the lysin or holin polypeptides, e.g., for Western blotting, imaging lysin or holin polypeptides in situ, measuring levels thereof in appropriate physiological samples, etc. using any of the detection techniques mentioned above or known in the art.

Bacterial Susceptibility to Lysin and Holin Activity

Any of the lysin activity tests described below may be performed to test the susceptibility of bacteria to lysin activity. Furthermore, any test which provides information as to the susceptibility of a cell wall of a bacterium of interest to the action of holin or lysin are suitable embodiments of the present invention. The present invention includes embodiments wherein the cell walls of any type of bacteria may be degraded by or tested for susceptibility to lysin. These embodiments may include *Staphylococcus aureus* or *Escherichia coli*, however preferred embodiments include streptococcus. Group A streptococcus, such as strain D471 and group C streptococcus, such as strain 26RP66 are especially preferred.

Lysin assays include, but are not limited to, bacterial viability testing, optical density measurements of a bacterial suspension, or color development using an artificial chromogenic substrate. The Example, infra, illustrates some of these assays.

It is expected that holin will be capable of penetrating the cell membranes of bacteria, such as group C and group A streptococci and others when they are exposed to the protein exogenously. Any test which provides data as to the ability of holin to penetrate a cell membrane of a bacterium of interest is a suitable embodiment of the present invention. Several possible assays for holin binding to bacterial cell membranes are suitable embodiments of the present invention. Methods to detect holin/cell membrane binding are disclosed above and any of these assays may be embodiments wherein the cell membranes of bacteria of interest may be evaluated for susceptibility to holin. Such assays include electrical conductance assays, osmotic lysis assays, molecular permeability assays, and the like.

Therapeutic Uses of Lysin or Holin

Lysin, as demonstrated in the Examples and observed previously, has potent antibiotic activity. It is particularly effective in topical bacterial lysis, e.g., in the oral cavity and at wound sites. Moreover, because lysin is specific for bacterial cell wall components, it will not impact host (human or other animal) functions as some potent antibiotics do. Furthermore, its specificity for group A, group C, and similar streptococci precludes destruction of the gastrointestinal flora, thus avoiding some of the gastrointestinal effects of broad spectrum oral antibiotics.

The antibiotic activity of lysin advantageously permits treatment of bacterial infection in any animal, particularly mammals, and more particularly humans. Other animals that can be treated include, but are not limited to, pets (dogs, cats, rodents, ferrets, etc.); laboratory animals (rats, mice, rabbits, hamsters, guinea pigs, etc.); farm animals; and wild animals, e.g., in a zoo.

The term "oral cavity" refers to any tissue which lines a cavity within the head and neck. These cavities include, but are not limited to, the nasal cavity, the throat, the mouth and the sinus cavities. Accordingly, a "bacterial oral cavity infection" or "bacterial oral infection" is a bacterial infection of an oral cavity. "Oral cavity bacteria" or "oral bacteria" are bacteria which are found in an oral cavity.

Lysin may be used therapeutically to inhibit the growth of bacteria comprising cell walls which are susceptible to the activity of lysin. The methods of this invention may also be applied prophylactically to prevent a patient from becoming sick after an exposure to a potentially infectious bacterium. Without being bound to a theory, this growth inhibition may occur by cleavage of the chemical bonds within the peptidoglycan structure of the bacterial cell wall. This cleavage may weakens the cell wall structure to physical and osmotic stresses, thereby increasing chances for cell wall rupture. This invention may include embodiments wherein bacterial infections of the nasal cavity, the throat, the mouth and the sinus cavities are treated, however, infections of other tissues in the head and neck area are also contemplated by the present application. Other methods which accomplish delivery of lysin containing compositions to any site of infection are also suitable and are possible embodiments of the present invention.

Lysin can also be used successfully prophylactically on medical instruments, e.g., as a sterilization agent. When applied to catheters, stents, artificial joins, pins, and other implanted devices, lysin prevents development of infections. In certain applications, lysin may be implanted by including recombinant cells that produce the protein in the device, e.g., for coronary or peripheral arterial shunts.

Furthermore, it is expected that the holin protein may provide a therapeutic or prophylactic effect. That is holin, when exposed to bacteria, may be capable of penetrating the bacterial cell membrane and causing an inhibition of growth. This inhibition may be the result of exposure of bacteria whose cell membranes have been penetrated by holin to endogenously produced bacterial cell wall degradative enzymes (autolysins). Autolysins are enzymes produced by bacteria which degrade peptidoglycan in a similar manner to lysin, for the purpose of facilitating the incorporation of new peptidoglycan into the growing cell wall.

In a preferred embodiment, the foregoing lysins and holins provide for prophylaxis and treatment of pneumonia, particularly in a hospital setting.

Formulations and Administration

The term "therapeutic agent" refers to any substance or composition of matter which causes a desired physiological effect when administered to a patient. For example, $C_1$ lysin is a therapeutic agent due to the fact that it inhibits bacterial growth in a patient to whom it is administered. Such physiological effects may include the inhibition of bacterial, fungal or viral growth or activity, pain alleviation or the alleviation of other physical maladies.

As shown in the Examples, to maintain its enzymatic activity, lysin should be kept in a reducing environment or in the presence of metal chelating compounds. Examples of such agents include dithiothreital (DTT), 2-mercaptoethanol (2-ME), cysteine, or glutathione, with the first two preferred. Chelators include EDTA and similar compounds.

Liquid preparations for oral administration can take the form of, for example, throat lozenges, mouth washes, injectants, aerosols, powders, pastes, gargles, solutions, syrups, elixirs, emulsions or suspensions, or they can be presented as a dry product for constitution with water or other suitable vehicle before use. Preparations for nasal administration may include injectants, aerosols, nasal sprays, nasal drops, nasal ointments, nasal washes, nasal injections, nasal packings. Ointments for direct application to nasal tissues are further possible embodiments. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Of particular utility are high viscosity preparations, such as syrups, comprising $C_1$ lysin. These preparations are taken orally and, due to their viscosity, remain in the oral cavity longer than preparations of a lower viscosity. A highly viscous liquid pharmaceutical preparation may be prepared using one or two or more of gelatin, pectin, xanthan gum, carrageenan or corn syrup to provide the desired level of thickness.

Preparations for oral administration can be suitably formulated to give controlled release of the active compound.

For buccal administration the therapeutics can take the form of tablets or lozenges formulated in conventional manner. The lozenge into which the lysin enzyme is added may contain any or all of the following ingredients: corn starch, acacia, gum tragacanth, anethole, linseed, oleoresin, mineral oil, and cellulose sugar, corn syrup, a variety of dyes, non-sugar sweeteners, flavorings, and any binders.

A chewable delivery system may be based on a nougat-type, chewy tablet. Such tablets generally employ a base of corn syrup (or a derivative). Such tablets are prepared as a confectionery, i.e., the corn syrup is cooked with water and a binder such as soy protein. One example of such a tablet is Tempo® antacid tablets, distributed by Thompson Medical Co., Inc., of West Palm Beach, Fla. Gum based formulations may also contain gum based products may contain any or all of the following ingredients: acacia, carnauba wax, citric acid, corn starch, food colorings, flavorings, non-sugar sweeteners, gelatin, glucose, glycerin, gum base, shellac, sodium saccharin, sugar, water, white wax, and cellulose and other binders.

For administration by inhalation, the therapeutics according to the present invention are conveniently delivered in the form of an aerosol spray presentation from pressurized packs or a nebulizer, with the use of a suitable propellant, e.g., (dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch. In order to accelerate treatment of the infection, the administration of a second therapeutic agent may be an embodiment of this invention. The second therapeutic agent may be administered to the patient as a part of the lysin composition or in the form of a separate composition which comprises only said second therapeutic agent. A non-limiting exemplary list of suitable second therapeutic agents includes penicillin, synthetic penicillins bacitracin, methicillin, cephalosporin, polymyxin, cefaclor.

Cefadroxil, cefamandole nafate, cefazolin, cefixime, cefinetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate, chelating agents and any combinations thereof in amounts which are effective to synergistically enhance the therapeutic effect of the lytic enzyme. Furthermore, antifingal compositions may be coadministered with the lysin containing compositions of this invention (separately or within the same composition as the lysin enzyme) Such antifungal agents may include Amphotericin B, Carbol-Fuchsin, Ciclopirox, Clotrimzole, Econazole, Haloprogin, Ketoconazole, Mafenide, Miconazole, Naftifine, Nystatin, Oxiconazole Silver, Sulfadiazine, Sulconazole, Terbinafine, Tioconazole, Tolnaftate, Undecylenic acid, flucytosine, miconazole, or others.

Compositions of the present invention may further comprise antiviral agents. Such antiviral agents may include zinc containing substances, such as zinc gluconate. Furthermore anesthetic agents may be included in the compositions of the present invention. Suitable anaesthetics may include aspirin, acetaminophen, phenol, benzocaine, diphenhydramine, kaolin-pectin and Xylocaine. Furthermore, decongestants and antihistamines may be included in compositions of the invention. Suitable decongestants may include pseudoephedrine, phenylpropanolamine and phenylephrine; antihistamines may include brompheniramine or chlorpheniramine.

Effective Dose

The compounds described herein can be administered to a patient at therapeutically effective doses to treat certain diseases or disorders. A therapeutically effective dose refers to that amount of a therapeutic sufficient to result in a healthful benefit in the treated subject. A prophylactically effective dose refers to that amount of a prophylactic sufficient to result in prevention of a disease in a patient.

The precise dose of the therapeutic embodied by this invention, to be employed in the formulation, will depend on the route of administration, and the nature of the patient's disease, and should be decided according to the judgment of the practitioner and each patient's circumstances according to standard clinical techniques. The term "inhibit" or "inhibition" means to reduce by a measurable amount. Experimental evidence of inhibition may include observing the elimination of a bacterial oral cavity infection in an animal model. Effective doses may thus be extrapolated from dose-response curves derived from animal model test systems.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutics that exhibit large therapeutic indices are preferred. While therapeutics that exhibit toxic side effects can be used, care should be taken to design a delivery system that targets such compounds to the site of affected tissue in order to minimize potential damage to uninfected cells and, thereby, reduce side effects.

The data obtained from the in vitro bacterial growth inhibition and cell lysis assays and animal studies can be used in formulating a range of dosage for use in humans. The dosage of lysin containing compositions lies preferably within a range of concentrations that include the $ED_{50}$ with little or no toxicity. The dosage can vary within this range depending upon the dosage form employed and the route of administration utilized. For any composition used in the method of the invention, the therapeutically effective dose can be estimated initially from in vitro bacterial growth inhibition and cell lysis assays. A dose can be formulated in animal models to achieve a lysin concentration range that includes the $IC_{50}$ (i.e., the concentration of the test compound which achieves a half-maximal inhibition of symptoms). Such information can be used to more accurately determine useful doses in humans. The efficacy of a particular dosage in eliminating, for example, a bacterial throat infection may be measured by a traditional throat culture swab assay. Any method which provides data as to the number of bacteria present at the site of infection would be suitable for these purposes.

In order to be effective, the enzyme should be present in an amount sufficient to provide an effective number of enzyme units in contact with the oral cavity. Having too few enzyme units in contact with the oral cavity, even over a long period of time, will not produce as beneficial an effect as desired. Hence, any dosage form employed should provide for an approximate minimum number of units for the amount of time that the dosage will provide enzyme to the oral cavity. The concentration of the active units of enzyme believed to provide for an effective amount or dosage of enzyme may be in the range of from about 100 units to about 100,000 units in the environment of the nasal and oral passages. Within that broader range, dosages of from about 100 units to about 10,000 units are believed to be acceptable. Such units can be contained in smaller volumes of carrier such as liquid or saliva, e.g. 1 ml or less (e.g. in the case of a lozenge) or can be contained in larger dosage volumes such as a gargle of several mls. Generally, therefore, larger volumes of carrier will require a greater total number of units to achieve an effective concentration of active enzyme. Hence, acceptable concentrations can be from about 100 units/ml to about 100,000 units/ml of fluid in the environment of the nasal or oral passages. Within this range, concentrations from about 100 units/ml to about 10,000 units/ml are acceptable.

In practice, therefore, the time exposure to the active enzyme units likely will influence the desired concentration of active enzyme units employed in the dosage per ml. For example, carriers that are considered to provide prolonged release (certain nasal sprays, lozenges and encapsulated enzyme) could provide a lower concentration of active enzyme units per ml, but over a longer period of time. Conversely, a shorter duration treatment (e.g., a gargle) could provide a higher concentration of active enzyme units per ml. Any dosage form containing sufficient lysin enzyme to provide effective concentrations of active enzyme at the site of infection or to provide a sufficient prophylactic effect are well within the bounds of routine experimentation and therefore, well within the scope of the instant invention.

Safety: Irritation Tests

The isolated lysin or holin proteins may be tested for the ability to irritate mucous membranes and skin. This test is performed so as to determine the suitability of administration of holin or lysin compositions to patients. These tests may be performed on any suitable animal, such as rabbits or hamsters. Any suitable site of application may be tested for irritation such as skin, vaginal mucous membranes, or oral mucous membranes. Detailed examples of said irritation tests are described below.

EXAMPLES

The invention may be better understood by reference to the following Examples, which is provided by way of exemplification and not limitation.

Example 1

Cloning, Sequencing, and Biochemistry of Homogeneously Purified Lysin

Since its discovery, several groups have partially purified the $C_1$ phage lysin, but none to homogeneity (Cohen et al., 1975; Raina, 1981). This Example describes purification and sequencing of this enzyme, and evaluation of the biochemical properties of highly purified lysin preparations. Due to the potential use of $C_1$ phage lysin as a prophylactic for the prevention and control of group A streptococcal pharyngitis, we investigated its long term stability, toxicology, and activity on normal oral microflora.

Materials and Methods

Unless otherwise indicated, all materials used were purchased from Sigma Chemical Company and were of the highest purity available.

Growth of Bacterial Strains.

Group C streptococcus 26RP66, group A streptococcus D471 (M-type 6), streptomycin resistant group A streptococcus T14/46 (M type 14), *Streptococcus gordonii* GP251, and *Staphylococcus aureus* 6390 were all from The Rockefeller University collection. Stock strains stored at −80° C. were routinely grown in THY (Todd-Hewitt broth, 1% w/v yeast extract (both from Difco)) or THY supplemented with 200 mg/ml streptomycin sulfate. For preparation of the $C_1$ bacteriophage and production of lysin, group C streptococcus was grown in chemically defined media (CDM) (JRH Biosciences).

Preparation of $C_1$ Bacteriophage.

The lytic bacteriophage, $C_1$, was part of The Rockefeller University Collection. In order to increase titers of the $C_1$ phage, group C streptococcal strain 26RP66 was grown at 37° C. to early log phase (preferably OD650~0.23) and 1/250 to 1/4 (v/v) of pre-warmed $C_1$ phage was added and allowed to incubate until complete lysis occurred (approximately 40 minutes). The lysate was passed through a 0.45 micron filter (Amicon) to sterilize the preparation and stored at 4° C. for future use.

Production of Lysin.

A starter culture (500 mls) of group C streptococcus 26RP66 was added to 10 L of CDM and incubated at 37° C. until the OD650~0.23, upon which 2 to 5 L of sterile lysate containing $C_1$ phage from above was added to infect the group C cells. At exactly 18 min of incubation at 37° C., 1 kg/L of ice was added to the infected group C cells to slow down phage replication. The iced culture was then centrifuged at 38,000 rpm on a Sharples centrifuge at a flow rate of approximately 0.2-0.5 L/min. The pellet containing infected group C cells was removed and suspended in approximately 50 mls of buffer containing enzyme buffer (EB) (5 mM phosphate buffer, 1 mM DTT, 1 mM EDTA, pH 6.1) which was supplemented with 1.25 mg DNase and allowed to incubate at 37° C. for an additional 30 minutes to complete replication and lysis. The concentrated crude lysin extract was stored at −80° C. until needed for purification.

Lysin Assay.

Three separate methods were utilized to detect lysin activity based on turbidimetric determination of cell lysis. In the first method, an overnight culture of group A streptococcus D471 was centrifuged (3000× g, 10 min), washed twice in EB, and the final OD650 was adjusted to 0.6 in the same buffer. Serial dilutions of lysin were made in EB in a final volume of 1 ml to which 1 ml of the freshly prepared group A cells were added and mixed. A control contained 1 ml of EB with one ml of group A cells. After incubation in a water bath at 37° C. for 15 min, the OD650 was measured for each dilution and the reciprocal of the highest dilution that was nearest to half of the control value is defined as the activity of lysin in U/ml. For example, if the mixture from a 1:6400 dilution produced a drop in OD650 from 0.30 to 0.15, then the enzymatic activity is 6400 units per ml. This method of detecting lysin activity was used in experiments where it was necessary to quantify exact lysin activity for yield determination.

A second method utilized 96 well plates (Costar) and an automated plate reader (Dynatech) for rapid determination of lysin activity. In this method, 25 ml of sample was mixed with 125 ml of EB and incubated at room temp for 5 min. Immediately before the assay was started, 100 ml of washed group A streptococcal D471 cells (OD650~1.0) was added to the desired wells. The 96 well plate reader allowed us to quantitate a total loss in OD650 by taking endpoint readings or measure kinetic data in terms of a decrease in mOD/min. The typical kinetic assay included measurements taken every 15 sec with 5 sec shaking each and read for 5 min. Unless lysin activity was very concentrated, the rate of lysis was linear over the 5 min assay period. This method was utilized to assay fractions from column chromatography steps as well as inhibitor and activation profiles for lysin. The third method to detect lysin activity was a modified diffusion plate assay.

Briefly, equal volumes of washed D471 cells (OD650 1.0) were mixed with a warm (50° C.) solution of 1% low diffusional agarose in water, poured into petri dishes, and allowed to cool. A final concentration of 0.5% agarose was found to allow maximal diffusion of lysin activity while retaining a solid gel structure. In this method, holes were punched in the agarose with the end of a Pasteur pipette and samples up to 25 ml could be spotted in each hole and incubated overnight at room temp or 37° C. and lysin activity was found to be proportional to the diameter of the clearing zone. Another application of this method involved using a native PAGE gel as an overlay which allowed us to identify the exact band responsible for lysin activity by comparison of an identical gel that had been Coomassie stained. Lysin Purification. 50 mls of concentrated crude extract was centrifuged (10,000× g, 20 min) to remove remaining bacterial debris and the clear supernatant was dialyzed against EB overnight with a 10 kDa MW cut-off membrane (Spectra-Por). The sample was then applied to a 15 ml HiTrap Q column (Amersham-Pharmacia Biotech) that had been equilibrated in EB and eluted in a linear gradient containing EB supplemented with 1 M NaCl. The fraction containing the activity was pooled, dialyzed against EB, and further purified by application to a hydroxylapatite column (Calbiochem), with elution in a linear gradient containing 1 M phosphate buffer, pH 6.1. Fractions containing activity were pooled, dialyzed, and concentrated (Amicon PM-10 membrane) to 10 mls and applied to an S-200 (16/60) column (Amersham-Pharmacia Biotech) equilibrated with EB supplemented with 200 mM NaCl.

Biochemical Characterization.

All biochemical characterization experiments utilized the standard 5 min 96 well plate assay, using 25 ml of lysin at a concentration of 1000 U/ml. For activation studies, lysin was preincubated for 5 min at room temperature with 5 mM phosphate buffer, 1 mM EDTA, pH 6.1 supplemented with either DTT, β-mercaptoethanol (Bio-Rad), L-cysteine, or glutathione at a final concentration of 10 mM. The lysin activity with these reducing compounds was expressed as a percentage of the activity in DTT, which was arbitrarily set to be 100%. Inhibition experiments utilized a similar scheme where lysin was preincubated for 5 min in the same buffer with the following sulfhydral reactive compounds at 1 mM final concentration: ethylmaleimide, dithiodipyridine, iodoacetamide, hydroxy mercuribenzoic acid (Calbiochem), iodoacetamide, and sodium tetrathionate. The same experiment was repeated with the exception that 10 mM DTT was added after the incubation with the inhibitors to assess reversibility of the inhibition. To investigate potential inhibitory effects of saliva, 25 ml of lysin was preincubated with 25-250 ml of human saliva for 5 min prior to assay. Lysin stability was investigated by supplementing EB of freshly purified lysin with 1 M phosphate buffer, 5% glycerol (Fisher), 20% glycerol, 1% mannose, 1% glucose, or 1% trehalose and adjusting the titer of each sample to 1000 U/ml. Samples were stored for 2 weeks at 4° C., and titered. Activity was expressed at a percentage of the starting activity.

Protein Sequencing.

Enzyme purification was monitored by native polyacrylamide gel electrophoresis (PAGE) using the Tris-HCl/Tricine buffer system (Schagger and von Jagow, 1987) and a 4-15% gradient gel (Bio-Rad). For protein sequence analysis, lysin was resolved by electrophoresis and electrotransferred onto a polyvinylidene difluoride (PVDF) membrane (Bio-Rad) according to Matsudaira (1987). Internal sequence analysis was performed by digesting the PVDF bound lysin with Lys-C, separating the peptides by reverse-phase HPLC, and sequencing the purified peaks. All digests and sequence analysis was performed at The Rockefeller University Protein/DNA Technology Center.

Sequencing the Lysin Gene.

Based on the N-terminal sequence (23 residues) of lysin, a pair of degenerate oligonucleotide primers (5'-AARATHAAYGTNAAYGT-3') (SEQ ID NO: 10) and (5'-TCYTTNCCRTCNGTRTG-3') (SEQ ID NO:1 1) corresponding to residues 1-6 (KINVNV) (SEQ ID NO: 12) and 18-23 (HTDGKE) (SEQ ID NO: 13), respectively, were designed. The DNA fragment coding for the N-terminus of lysin was amplified by PCR using Taq DNA polymerase (Perkin Elmer) and 10 ng of $C_1$ phage genomic DNA (purified by using the Lambda Phage Purification Kit, Qiagen). PCR was carried out with 500 ng of primers for 1 min at 94° C., 1 min at 55° C., and 20 sec. at 72° C. for 25 cycles. The expected 75 bp PCR product was cloned using the TA Cloning Kit (Invitrogen) and sequenced using universal M13 primers. From the cloned sequence, non-degenerative forward and reverse primers were designed, and the gene for lysin was directly sequenced by chromosomal walking using the purified 17 kb genomic $C_1$ phage DNA as the template. All sequencing was carried out at The Rockefeller University Protein/DNA Technology Center.

Lysin Irritation Tests.

Crude and purified lysin were diluted to 1000 U/ml and sterilized by passing through a 0.45 micron filter (Amicon) and sent to the STS Testing Company in Rush, N.Y. for testing of skin and rabbit vaginal mucous membrane irritation. Additionally, samples were sent to MB Research Laboratories in Spinnerstown, Pa. for Hamster cheek-pouch buccal mucosal irritation testing.

To assess vaginal mucous membrane irritation, healthy, albino, white rabbits ((NZw)SPF) were given EB control (n=6) or one human dose (1000 U) of crude lysin (n=6) or pure lysin (n=6) vaginally for 5 consecutive days. Each rabbit was then euthanized and the vaginal tissue was removed and evaluated by a veterinary histopathologist who assigned a composite index score for each animal based on the status of the epithelium, vascular congestion, leukocyte infiltration, and edema. Maximal irritation is defined as an index score of 16.0 and any index score <4.0 indicates the lowest minimal irritation.

The hamster cheek-pouch buccal test offered an additional mucosal membrane to test for sensitivity. Fifteen healthy male Golden Syrian hamsters were assigned to three groups of five animals/group. Group 1 served as a sham treated control and received no sample. Group 2 was given 0.5 ml of crude lysin applied to the buccal mucosa of the left cheek pouch twice daily for 5 days and Group 2 was given 0.5 ml of purified lysin twice daily for 5 days. Erythema and edema were scored prior to each treatment and the Group Average Mucosal Irritation scores were calculated.

In order to assess skin irritation, six ((NZw)SPF) rabbits were shaved and crude lysin, pure lysin, or control was applied by patch to intact and abraded skin sites. Adjacent areas of skin on each animal served as a control. After 24 hours, the patches were removed and examined for signs of erythema and edema 24 and 72 hours subsequent to patch removal. The average values of the six rabbits for erythema and edema formation were added to derived a Primary Irritation Index (PII). The PII has a maximal value of 8.0 and any value <5.0 is not considered to be a positive irritant.

Lysin Activity on Various Bacterial Strains.

Group A streptococcus D47 1, group C streptococcus 26RP66, *Streptococcus gordonii* GP251, and *Staphylococcus aureus* 6390 were grown in THY overnight at 37° C., washed twice in EB, and the OD650 was adjusted to 1.0 prior to addition of crude or purified lysin (25 ml at a concentration of 1000 U/ml) in a 96 well plate. After 10 min incubation at room temperature with constant shaking, an endpoint OD650 was measured to quantify cell lysis.

Electron Microscopy.

$C_1$ phage particles were pelleted by ultracentrifugation (100,000× g, 2 hours) and processed by The Rockefeller University Electron Microscopy Facility for visualization of the phage structure by negative stain and thin section analysis.

Results

Lysin Purification.

Lysin from $C_1$ phage lysates of group C streptococcus 26RP66 was purified by HiTrap Q ion exchange, hydroxylapatite affinity, and S-200 gel filtration chromatography. A single migrating band on native PAGE was shown to contain muralytic activity by an overlay assay (data not shown). Purified lysin excised from the gel was sent to The Rockefeller University Protein/DNA Technology Center for N-terminal and internal protein sequencing which yielded four distinct peptide sequences (Table 1). Lysin had an observed molecular weight of 100 kDa, which is consistent with previously published reports (Fischetti et al., 1971; Raina, 1981).

TABLE 1

Peptides from Lysin

| | | |
|---|---|---|
| N-terminal sequence KINVNVENVSGVQFLFHTDGKE | (SEQ ID NO:5) | |
| Peptide-1 DIETVQGFQQIIPSINISK | (SEQ ID NO:6) | |
| Peptide-2 XXYGYRAF | (SEQ ID NO:7) | |
| Peptide-3 XDVEAIRK | (SEQ ID NO:8) | |

Lysin Stability and Inhibition.

Lysin rapidly looses activity if not stored in the presence of reducing agents and/or metal chelating agents. At 10 mM concentrations, both DTT and β-mercaptoethanol were slightly better activators of lysin compared to cysteine or glutathione (FIG. 1). However, at 1 mM concentrations that were routinely used in purification and assay buffers, little detectable difference was noticed between these reducing agents.

Figure 2:
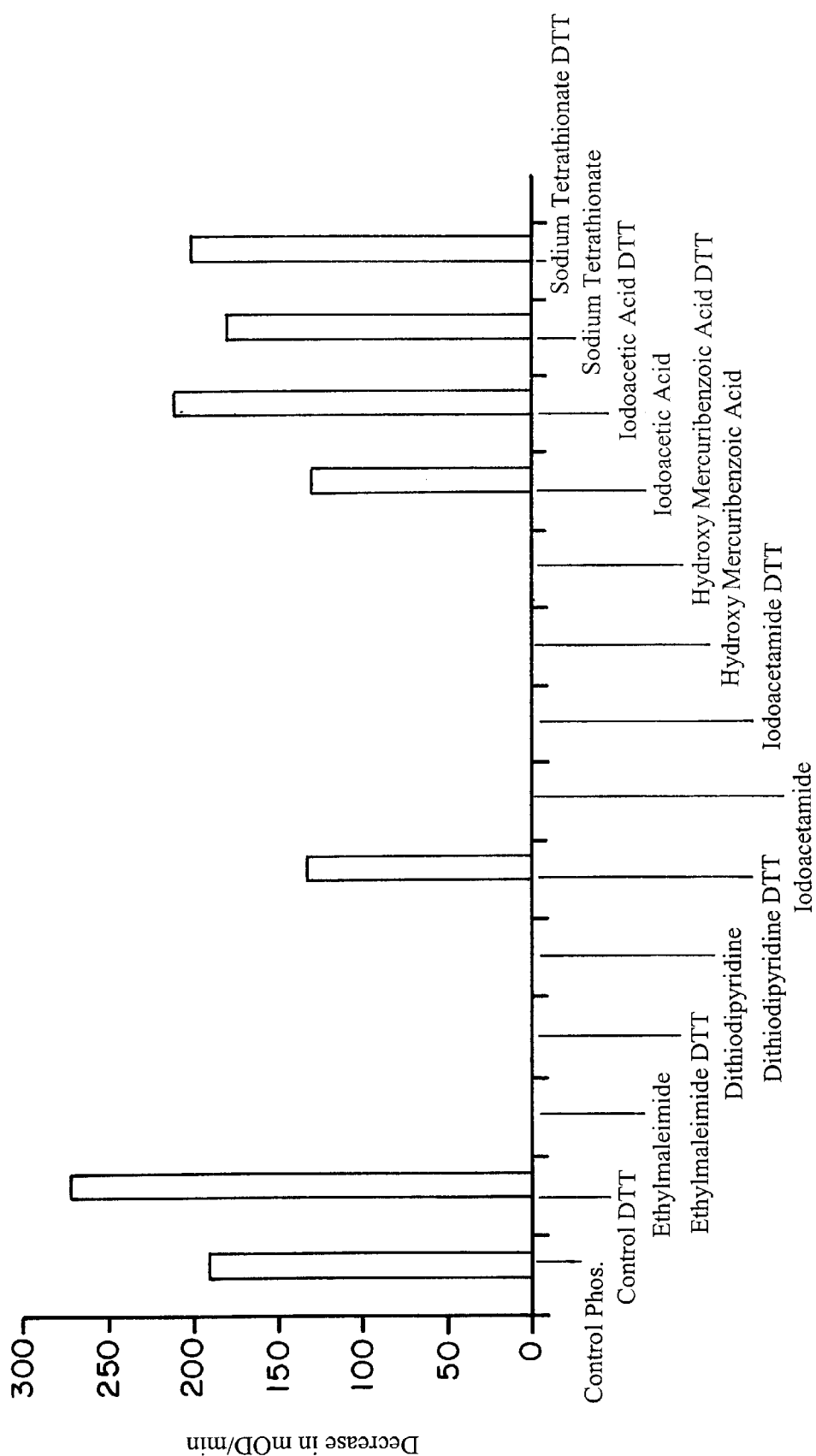
FIG. 2. Various sulfhydral reactive compounds were tested with and without the addition of excess DTT to assess the reversibility of these inhibitors.

Given the importance of reducing agents to the activity of lysin, we assayed various sulfhydral reactive compounds for the ability to inhibit lysin (FIG. 2). As expected, ethylmaleimide, iodoacetamide, and hydroxy mercuribenzoic acid were all strong irreversible inhibitors of lysin, and dithiopyridine was a reversible inhibitor. Surprisingly, iodoacetic acid had only a slight inhibitory effect and sodium tetrathionate had no inhibitory capacity, which is contrast to previously published reports (Fischetti et al., 1971).

Because lysin is intended for use in the oral cavity, we tested lysin in the presence of increasing concentrations of human saliva to mimic in vivo conditions (FIG. 3). As can be seen, human saliva contains no natural lysin inhibitors.

Even in the presence of reducing agents and EDTA, purified lysin lost appreciable activity after several days at 4° C., presumably due to being a dilute protein solution. To address long term stabilization of lysin, we tested this enzyme in the presence of several sugars, all of which helped stabilize the enzyme over a two week period with 20% glycerol being the best stabilizer (FIG. 4). Interestingly, semi purified lysin fractions in high phosphate buffer (>0.5M) lost no activity over two weeks, and we have noticed similar stability for several months in high phosphate buffer (data not shown).

Lysin Gene Sequencing.

Figure 5:
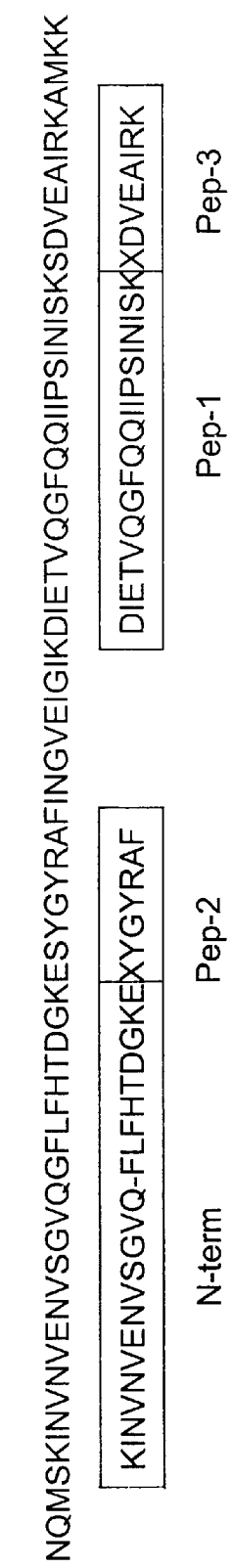
FIG. 5. Comparison of the peptide sequence data obtained by direct peptide sequencing (SEQ ID NOS:5, 6, 7, 8) with the amino acid sequence deduced from the cloned lysin gene (SEQ ID NO:2).

The $C_1$ phage genome was purified and found to be about 17 kb and have a restriction digest pattern similar to previously published reports (data not shown) (Pomrenke and Ferretti, 1989; Totolian et al., 1981). After we cloned the N-terminal fragment and identified a non-degenerative sequence, chromosomal walking allowed us to sequence the gene for lysin directly using genomic DNA as the template. The gene for lysin is 222 nucleotides (SEQ ID NO: 1) which corresponds to 74 amino acids (SEQ ID NO:2) giving lysin a predicted molecular weight of 8.4 kDa. Significantly, the lysin protein sequence from direct sequencing aligns nearly identically to the predicted protein sequence determined from the DNA sequence (FIG. 5). Additional DNA sequencing by chromosomal walking identified a putative holin gene (SEQ ID NO:3) directly upstream of the lysin gene. Holin and endolysins comprise the lytic system of phages.

Lysin Safety and Toxicity.

Figure 6:
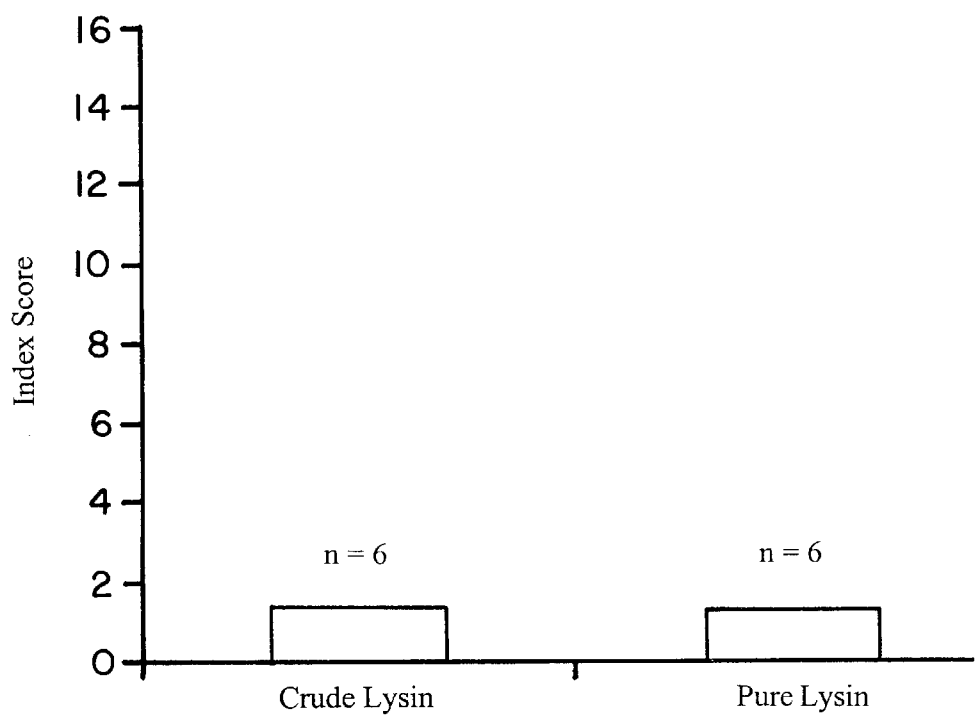
FIG. 6. Irritation scores for crude and pure lysin in a rabbit vaginal mucous membrane test.
Figure 7:
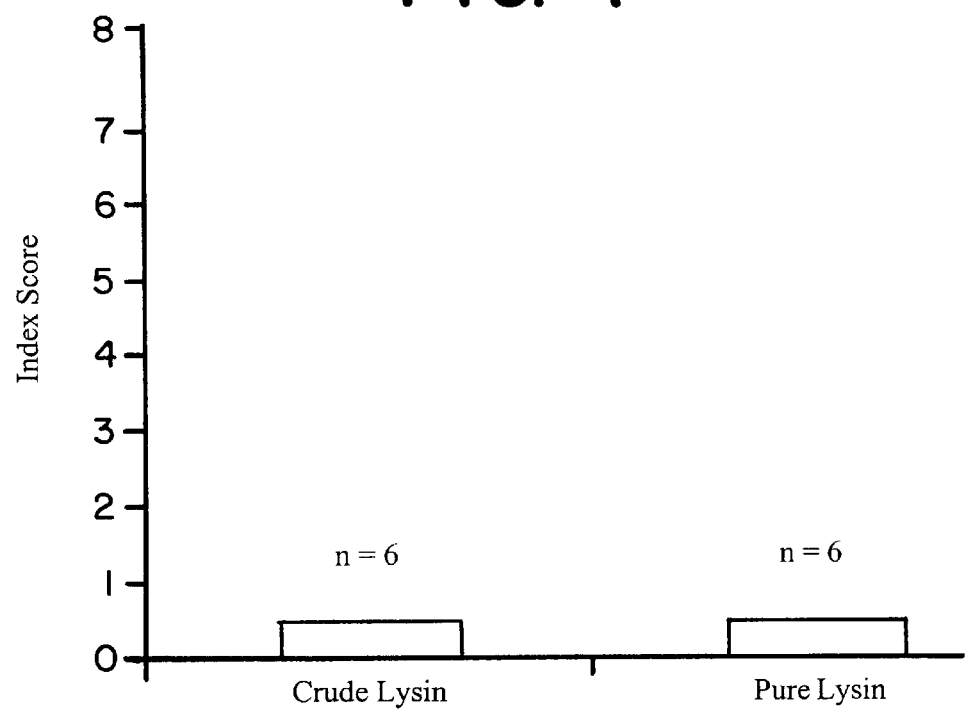
FIG. 7. Irritation scores for crude and pure lysin in a rabbit skin irritation test.

Crude and purified lysin samples were sent to two contract laboratory for irritation testing on both mucous membranes and skin. A rabbit vaginal irritation index that tested the appearance of the epithelium, vascular congestion, leukocyte infiltration, and edema rated both crude and purified lysin as being a "lowest minimal irritant" (FIG. 6). Likewise, a hamster cheek-pouch buccal mucosal irritation study showed no irritation on each of five consecutive days of treatment (Table 2). A rabbit skin irritation occlusive patch technique that monitored erythema and edema rated both crude and purified lysin as being a "non-irritant" (FIG. 7).

TABLE 2

Irritation Scores

| | Day 1 | Day 2 | Day 3 | Day 4 | Day 5 |
|---|---|---|---|---|---|
| Sham Control | 0 | 0 | 0 | 0 | 0 |
| Crude Lysin | 0 | 0 | 0 | 0 | 0 |
| Purified Lysin | 0 | 0 | 0 | 0 | 0 |

Bacterial Specificity.

Figure 8:
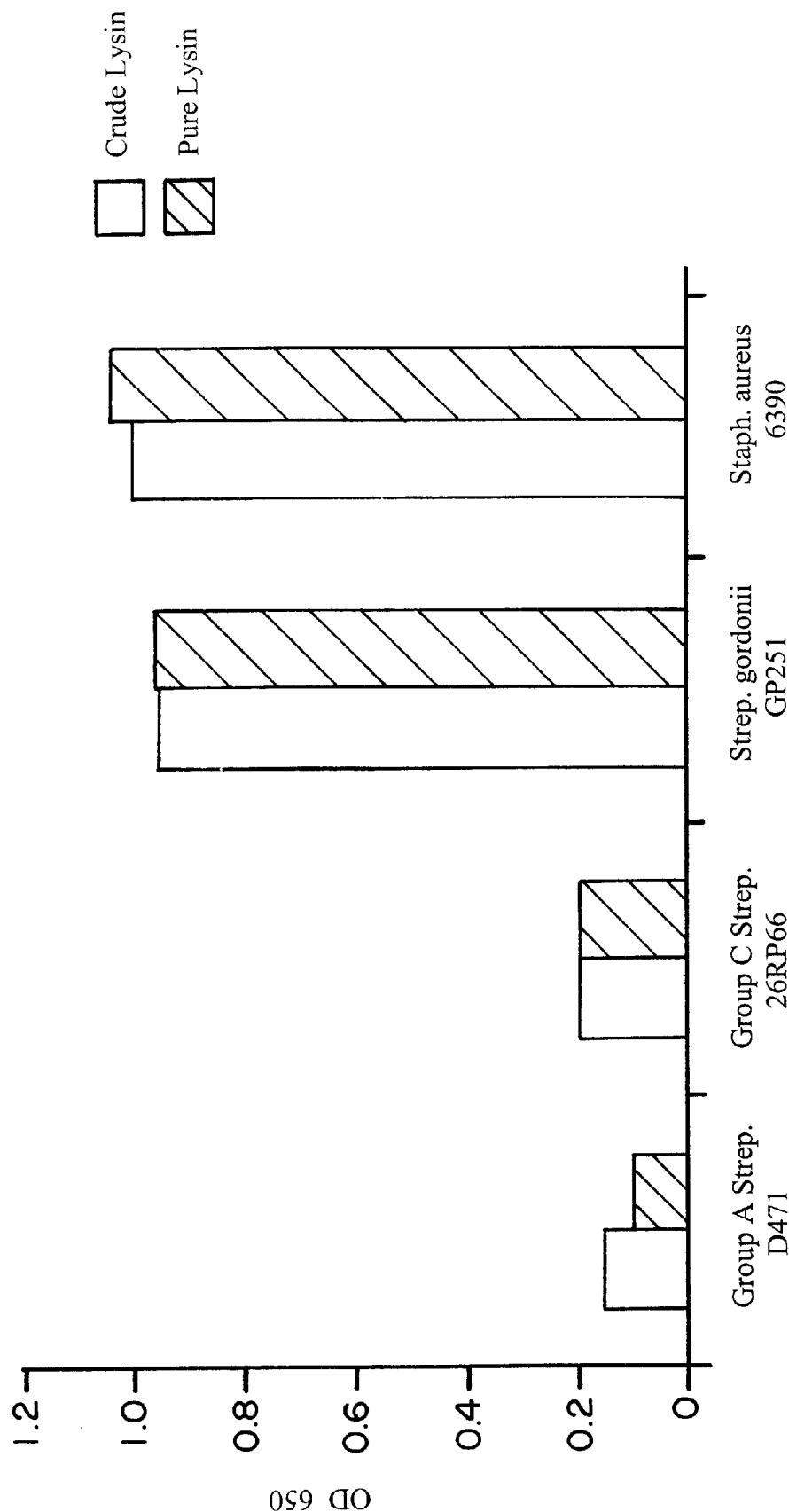
FIG. 8. Lysin activity on various bacterial strains.

Lysin's cells wall specificity was determined by testing the ability of lysin to degrade the cell wall of several oral bacteria (FIG. 8). As expected, both crude and purified lysin lysed group A streptococcus D471 and group C streptococcus 26RP66 cells to near completion within 10 min, but had no effect on *Staph. aureus* 6390 cells. Interestingly, lysin did appear to have very minor activity against *Strep. gordonii* GP251 cells after 10 minutes. After 5 hours of incubation with *S. gordonii* GP251, the OD650 had dropped to 0.5 from the starting value of 1.0 (data not shown).

Electron Microscopy of $C_1$ Phage.

Electron microscopy revealed the $C_1$ bacteriophage to have an polyhedron head approximately 45 by 45 nm, a base plate, and several short tail fibers with greater resolution than previously reported (Moynet et al., 1985; Vereanu et al., 1977). The physical properties of the $C_1$ phage most resemble those of the order Caudovirales and the family Podoviridae (viruses with short non-contractile tails) which include the T7 phage, P22 phage, and f29 phage. In addition to the physical similarities revealed by electron microscopy, the virulent, lytic method of infection by the $C_1$ phage, small genome size determined by us and others (Pomrenke and Ferretti, 1989), and presence of double stranded, non-permuted DNA (Totolian et al., 1981), are all consistent with the other members of the Podoviridae family (Maniloff and Ackermann, 1998). It is our recommendation that the $C_1$ phage be added as the fourth member to this family.

Discussion

Crude $C_1$ phage lysin preparations have been used for decades as a tool to extract cell wall associated molecules or to lyse cells for DNA purification from group A streptococci. However, despite being identified over 40 years ago, there has been no report of a complete purification of the $C_1$ phage lysin to homogeneity. Because the crude enzyme can be diluted several thousand fold, thereby diluting contaminating proteins while still possessing enough muralytic activity to rapidly lyse group A streptococci, there has been a general lack of interest in attempting to purify this enzyme. Additionally, the instability of the $C_1$ lysin has further complicated attempts to purify this enzyme. Notwithstanding, several groups have reported partial purification and characterization of the $C_1$ lysin, all of which show an approximate molecular weight of 100 kDa, and the requirement for a reducing environment and/or metal chelation for activity (Cohen et al., 1975; Fischetti et al., 1971; Raina, 1981).

Our results confirm that the native enzyme has an apparent molecular weight of about 100 kDa by gel filtration. However, sequencing of the lysin gene indicates that it is only 8.4 kDa, suggesting that native lysin forms a complex with itself and/or other proteins. Additionally, the lysin protein sequence does not contain any cysteine residues, which would be expected based on the sensitivity of this enzyme to sulfhydral reactive compounds. Therefore, it should not be ruled out that additional sequencing of the $C_1$ genome will yield proteins associated with the lysin protein upstream of the lysin start codon or downstream of the stop codon. Significantly, many phage lytic systems are characterized by multiple start codons producing proteins of various sizes (Young, 1992), as well as lytic enzymes fully embedded out of frame in endolysin genes (Loessner et al., 1999). Indeed, shifting the reading frame +1, we noted an open reading fame encoding a putative holin gene immediately upstream of the lysin gene. Moreover, it has been reported that a S. aureus autolysin contains both an amidase domain and an acetylglucosaminidase domain yielding a protein with a molecular size of 137 kDa (Oshida et al., 1995). One or several of the above circumstances may explain the noted size discrepancy of the gene sequence for lysin and the apparent native size of this protein.

Our results confirm the work of others showing that $C_1$ phage lysin is as specific for group A streptococcal cell walls as it is for group C streptococcal cell walls (Krause, 1957; Maxted, 1957). We additionally showed that lysin has no effect on other representative Gram positive bacteria, as well as having barely detectable activity (<0.1% of group A streptococci activity) on closely related viridans streptococci. Additionally, toxicology and irritation studies at contracted laboratories show lysin to be a non-irritant at predicted human doses. Taken together, these results suggest that lysin may be a potential therapeutic for prevention or management of group A streptococcus pharyngitis that is both safe and non-detrimental to the normal oral microflora.

Example 2
Detection of Streptococci

In accordance with the current invention, the presence of the group A or C streptococcal antigen in the extracting reagent is detected by an antigen-antibody reaction (immunoassay) wherein the antibody is labelled with an indicator particle or molecule. A specific, non-limiting example of this assay is herein described.

The lysin enzyme may be purified by methods described in Example 1 and later used in streptococcal detection assays. Use of the enzyme in an immunodiagnostic assay requires a minimum number of units of substantially pure lysin enzyme per test depending on the incubation times required. The enzyme is diluted in a stabilizing buffer containing the appropriate conditions for stability, maximum enzymatic activity, inhibitors of nonspecific reactions, and in some configurations contains specific antibodies to the Group A or group C carbohydrate. The preferred embodiment is to use a lyophilized reagent which can be reconstituted with water. The stabilizing buffer can comprise a reducing reagent, which can be dithiothreitol in a concentration from 0.001M to 1.0M, preferably 0.005M. The stabilizing buffer can comprise a metal chelating reagent, which can be ethylenediaminetetraacetic acid disodium salt in a concentration from 0.00001M to 1.0M, preferably 0.005M. The stabilizing buffer can comprise an immunoglobulin or immunoglobulin fragments in a concentration of 0.001 percent to 10 percent, preferably 0.1 percent. The stabilizing buffer can comprise a citrate-phosphate buffer in a concentration from 0.001M to 1.OM, preferably 0.05M. The stabilizing buffer can have a pH value in the range from 5.0 to 9.0, preferably 6.1. The stabilizing buffer can comprise a bactericidal or bacteriostatic reagent as a preservative. Such preservative can be sodium azide in a concentration from 0.001 percent to 0.1 percent, preferably 0.02 percent. Homogeneously purified lysin enzyme is diluted to a concentration of 100 units/ml in a buffer consisting of 0.05M citrate phosphate buffer pH 6.1 containing 0.1% rabbit immunoglobulin, 0.005M (ethylenedinitrilo) tetraacetic acid disodium salt (EDTA), 0.005M Dithiothreitol, 0.02% sodium azide, 0.01% Nacetylglucosamine. One part colloidal gold sol labelled with Group A or group C Streptococcal Antibody ($OD_{520}$ 1.5) suspended in 0.02M Tris 2 buffer pH 8.2, 1.0% bovine serum albumin, 0.02% sodium azide, 300K units heparin, is added to 3 parts of the enzyme reagent, mixed, filtered through a 0.22 micron filter, and 200 microliters aliquoted per tube and lyophilized. This lyophilized reagent is stable at elevated temperatures (i.e. 45° C.) for short term conditions (i.e. 2 weeks) and long term storage at room temperatures (>1 year). A rayon or dacron swab, preferably dry, is used to swab the suspected infected area. Two hundred microliters of deionized water is added to a reaction tube containing the lyophilized chromophore—enzyme mixture and the swab is added and twirled to mix the reagents. After a 4 minute incubation at room temperature, the swab is placed on a device consisting of a 1.2 micron cellulose acetate filter which is situated on top of a plastic laminate containing 2 holes, that are each 1.5 mm in diameter. Below one well is fixed a detection membrane saturated with rabbit anti Streptococcal Group A or group C capture antibody and under the other a control membrane saturated with rabbit non-immune immunoglobulin. Both membranes are situated on top of an absorbant paper to draw any excess fluid from the swab thru the membranes. If Group A or group C Antigen is present, the immune complex is deposited and captured on the detection membrane and a pink to black color can be visualized on the detection membrane. In the absence of Group A or group C Streptococcal Antigen the chromophore labelled antibody diffuses through the membrane and is not visible on that membrane. Using swabs seeded with Group A or group C Streptococci it is possible to detect $2 \times 10^4$ organisms in less than five minutes. The addition of heparin, 0.01% N-acetyl glucosamine, 0.1% rabbit immunoglobulin and a 1-2 micron filter overlay are necessary to reduce the occurrence of nonspecific reactions encountered in clinical throat specimens.

In another embodiment for the detection of group A or group C streptococci, the lysin extraction reagent is typically provided in lyophilized form for on site reconstitution. Before reconstitution the extraction reagent maybe stored refrigerated (2° to 8° C.) for at least 30 days without any significant loss of enzyme activity. Reconstituted extraction reagent is dispensed (typically 200 microliters). The throat swab is placed in the sample cup and incubated for at least 2 minutes at room temperature to allow the enzyme to free the streptococcal cell wall antigens from the swab fibers. After the incubation period, the swab is rotated and squeezed against the wall of the sample cup to express the fluid. An aliquot of the fluid can then be tested in an immunoassay, such as latex agglutination.

In accordance with the current invention, the ideal embodiment for the detection of the Group A or group C Streptococcal antigen is a chromophore labelled membrane spot test.

It should be understood that the identification of the group A or group C antigen released by the lysin enzyme is not limited to the identification method outlined above. The detection method may be substituted by any immune detection system such as antibody—bound latex particles, radioimmunoassay, immunofluorescence techniques, enzyme linked immunosorbant assay (ELISA) etc.

It should also be understood that the antigen to be detected is not limited to the group A or group C carbohydrate. Since other cell wall antigens are released during the digestion process (i.e. M Protein) antibody detection of these antigens may also be used in the identification of the group A streptococcus.

According to the invention, the test kit will utilize suitable applicator swabs for specimen transfer. The enzyme-containing extraction reagent will be provided in lyophilized form for on-site reconstitution. After reconstitution, the extraction reagent may be maintained at refrigerator temperature (2°-10° C.) for greater than 5 weeks.

REFERENCES

Cohen, J. O., Gross, H., and Harrell, W. K. (1977). Immunogenicity and Characteristics of M Protein Released by Phage-Associated Lysin from Group A Streptococci Types 1 and 23. J. Med. Microbiol. 10, 179-194.

Cohen, J. O., Gross, H., and Harrell, W. K. (1975). Simple Procedure for Production by Group C Streptococci of Phage-Associated Lysin Active Against Group A Streptococci. Appl. Microbiol. 29, 175-178.

Evans, A. C. (1934). Streptococcus Bacteriophage: A Study of Four Serological Types. Public Health Reports 49, 1386-1388.

Fischetti, V. A., Gotschlich, E. C., and Bernheimer, A. W. (1971). Purification and Physical Properties of Group C Streptococcal Phage-Associated Lysin. J. Exp. Med. 133, 1105-1117.

Fischetti, V. A., Jones, K. F., and Scott, J. R. (1985). Size Variation of the M Protein in Group A Streptococci. J. Exp. Med. 161, 1384-1401.

Krause, R. M. (1957). Studies on Bacteriophages of Hemolytic Streptococci. I. Factors Influencing the Interaction of Phage and Susceptible Host Cells. J. Exp. Med. 108, 365-384.

Loessner, M. J., Gaeng, S., and Scherer, S. (1999). Evidence for a Holin-Like Protein Gene Fully Embedded Out of Frame in the Endolysin Gene of Staphylococcus aureus Bacteriophage 187. J. Bacteriol. 181, 4452-4460.

Maniloff, J., and Ackermann, H. W. (1998). Taxonomy of Bacterial Viruses: Establishment of Tailed Virus Genera and the Order Caudovirales. Arch. Virol. 143, 2051-2062.

Matsudaira, P. (1987). Sequence from Picomole Quantities of Proteins Electroblotted onto Polyvinylidene Difluoride Membranes. J. Biol. Chem. 262, 10035-10038.

Maxted, W. R. (1957). The Active Agent in Nascent Phage Lysis of Streptococci. J. Gen. Microbiol. 16, 584-594.

Moynet, D. J., Colon-Whitt, A. E., Calandra, G. B., and Cole, R. M. (1985). Structure of Eight Streptococcal Bacteriophages. Virology 142, 263-269.

Oshida, T., Sugai, M., Komatsuzawa, H., Hong, Y. -M., Suginaka, H., and Tomasz, A. (1995). A Staphylococcus aureus Autolysin that has an N-Acetylmuramoyl-L-Alanine Amidase Domain and an Endo-B-N-Acetylglucosaminidase Domain: Cloning, Sequence Analysis, and Characterization. Proc. Natl. Acad. Sci. USA 92, 285-289.

Pomrenke, M. E., and Ferretti, J. J. (1989). Physical Maps of the Streptococcal Bacteriophage A25 and $C_1$ Genomes. J. Basic Microbiol. 6, 395-398.

Raina, J. L. (1981). Purification of Streptococcus Group C Bacteriophage Lysin. J. Bacteriol. 145, 661-663.

Schagger, H., and von Jagow, G. (1987). Tricine-Sodium Dodecyl Sulfate-Polyacrylamide Gel Electrophoresis for the Separation of Proteins in the Range from 1 to 100 kDa. Anal. Biochem. 166, 368-379.

Totolian, A. A., Gupalova, T., Coll, J., Suvorov, A., Boitsov, A., and Golubkov, V. I. (1981). Introduction to the Molecular Biology of Virulent Streptococcal Bacteriophages. In Basic Concepts of Streptococci and Streptococcal Diseases, S. Holm and P. Christensen, eds. (Surrey: Reedbooks Ltd.), pp. 231-233. Vereanu, A., Mihalcu, F., and Ionescu, M. D. (1977). Morphological Characters of Group A and Group C Streptococcal Bacteriophages. Arch. Roum. Pathol. Exp. Microbiol. 36, 29-35.

Wheeler, J., Holland, J., Terry, J. M., and Blainey, J. D. (1980). Production of Group C Streptococcus Phage-Associated Lysin and the Preparation of Streptococcus pyogenes Protoplast Membranes. J. Gen. Microbiol. 120, 27-33.

Young, R. (1992). Bacteriophage Lysis: Mechanism and Regulation. Microbiol. Rev. 56, 430-481.

Young, R., Wang, I. -N., and Roof, W. D. (2000). Phages Will Out: Strategies of Host Cell Lysis. Trends Microbiol. 8, 120-128.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all values are approximate, and are provided for description.

All patents, applications, publications, test methods, literature, and other materials cited herein are hereby incorporated by reference.

What is claimed:

1. An isolated nucleic acid encoding a $C_1$ bacteriophage holin polypeptide, wherein the polypeptide comprises an amino acid sequence which is at least about 70% identical to the amino acid sequence as set forth in SEQ ID NO:4 and the polypeptide is able to penetrate the inner membrane of streptococcal bacteria.

2. The isolated nucleic acid of claim 1 coding a polypeptide V mprising an amino acid sequence that is at least about 80% identical to the amino acid sequence as set forth in SEQ ID NO:4.

3. The isolated nucleic acid of claim 2 encoding a polypeptide comprising an amino acid sequence that is at least about 90% identical to the amino acid sequence as set forth in SEQ ID NO:4.

4. The isolated nucleic acid of claim 3 coding a polypeptide which has an amino acid sequence as set forth in SEQ ID NO:4.

5. The nucleic acid of claim 1, comprising a nuoleotide sequence which is at least about 70% identical to the nucleotide sequence as set in SEQ ID NO:3.

6. The isolated nucleic acid of claim 5 comprising a nucleotide sequence which is at least about 80% identical to the nucleotide sequence as set forth in SEQ ID NO:3.

7. The isolated nucleic acid of claim 6 comprising a nucleotide sequence which is at least about 90% identical to the nucleotide sequence as set forth in SEQ ID N0:3.

8. The nucleic acid of claim 5 which has a nucleotide sequence as set forth in SEQ ID NO:3.

9. An expression vector comprising the nucleic acid of claim 1 operabiy associated with a promoter.

10. A host cell comprising the vector of claim 9.

11. A method for producing a $C_1$ holin, which method comprises culturing the host cell of claim 10, under conditions that permit expression of the $C_1$ holin from the expression vector.

12. The method of claim 11 which further comprises purifying the $C_1$ holin to homogeneity.

* * * * *